(12) United States Patent
Ban et al.

(10) Patent No.: US 7,302,398 B2
(45) Date of Patent: Nov. 27, 2007

(54) HEALTH MANAGEMENT SUPPORT METHOD, SYSTEM AND HEALTHY LIFE EXPECTANCY PREDICTION DATA GENERATION METHOD AND SYSTEM

(75) Inventors: Hideyuki Ban, Hachioji (JP); Hiroyuki Kuriyama, Kawasaki (JP); Hitoshi Matsuo, Musashino (JP); Kuniaki Minami, Sakura (JP); Tsutomu Sakuma, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 725 days.

(21) Appl. No.: 10/078,475

(22) Filed: Feb. 21, 2002

(65) Prior Publication Data
US 2003/0101075 A1 May 29, 2003

(30) Foreign Application Priority Data
Nov. 29, 2001 (JP) ............... 2001-363564

(51) Int. Cl.
*G06Q 50/00* (2006.01)
(52) U.S. Cl. .............................. 705/2; 705/3
(58) Field of Classification Search ................ 705/2–3; 600/300, 301
See application file for complete search history.

(56) References Cited

U.S. PATENT DOCUMENTS

| | | | | |
|---|---|---|---|---|
| 5,018,067 A | * | 5/1991 | Mohlenbrock et al. | 600/300 |
| 5,301,105 A | * | 4/1994 | Cummings, Jr. | 705/2 |
| 5,557,514 A | * | 9/1996 | Seare et al. | 705/2 |
| 5,613,072 A | * | 3/1997 | Hammond et al. | 705/4 |
| 5,692,501 A | * | 12/1997 | Minturn | 600/301 |
| 5,778,345 A | * | 7/1998 | McCartney | 705/2 |
| 5,819,228 A | * | 10/1998 | Spiro | 705/2 |
| 5,937,387 A | * | 8/1999 | Summerell et al. | 705/2 |
| 6,044,351 A | * | 3/2000 | Jones | 705/2 |
| 6,059,724 A | * | 5/2000 | Campell et al. | 600/300 |
| 6,110,109 A | * | 8/2000 | Hu et al. | 600/300 |
| 6,269,339 B1 | * | 7/2001 | Silver | 705/2 |
| 6,283,761 B1 | * | 9/2001 | Joao | 434/236 |

(Continued)

FOREIGN PATENT DOCUMENTS

EP 917078 A1 * 5/1999

(Continued)

OTHER PUBLICATIONS

Smith, V. Kerry "Longevity Expectations and Death: Can People Predict Their Own Demise?" Sep. 2001. The American Economic Review. vol. 91, Iss. 4. pp. 1126.*

(Continued)

*Primary Examiner*—C. Luke Gilligan
*Assistant Examiner*—Michael Tomaszewski
(74) *Attorney, Agent, or Firm*—Reed Smith LLP; Stanley P. Fisher, Esq.; Juan Carlos A. Marquez, Esq.

(57) ABSTRACT

It was difficult for previous health management support systems to grasp daily health condition quantitatively through using comprehensive indexes of personal health conditions, optimize advice as healthcare guidance, and show its expected effect in a favorable way. The disclosed method and system implement the following: estimating a predicted period of healthy life expectancy of each person who underwent health screening from health screening report data obtained through the health screening report data entry step, wherein healthy life expectancy prediction data is used that is prepared as basic data for predicting healthy life expectancy from a diversity of health screening report data. The predicted period of healthy life expectancy and related information for each person are displayed by display means or printed out by printing means.

20 Claims, 22 Drawing Sheets

U.S. PATENT DOCUMENTS

| | | | |
|---|---|---|---|
| 6,458,080 B1 * | 10/2002 | Brown et al. | 600/300 |
| 6,527,712 B1 * | 3/2003 | Brown et al. | 600/300 |
| 6,547,729 B1 * | 4/2003 | Abbo | 600/300 |
| 6,569,093 B2 * | 5/2003 | Iliff | 600/300 |

FOREIGN PATENT DOCUMENTS

| | | | |
|---|---|---|---|
| JP | 2001067403 A | * | 3/2001 |

OTHER PUBLICATIONS

Erfurt, John C. "The Cost-Effectivenes of Worksite Wellness Programs for Hypertension Control, Weight Loss, Smoking Cessation, and Exercise" Spring 1992. vol. 45, Iss. 1. pp. 5 and 23.*

Jagger, Carol. "Health Expectancy Calculation by the Sullivan Method" Jun. 13, 2001.*

Saloman, Joshua. Mathers, Colin D. Murray, Christopher JL. Ferguson, Brodie. "Methods for life expectancy and healthy life expectancy uncertainty analysis" Aug. 2001. World Health Organization.*

Scientific Institute of Public Health. "Healthy Ageing" Jun. 26, 2000. @ http://www.iph.fgov.be/epidemio/epien/PROG18.HTM.*

International Union for the Scientific Study of Popluation. "Longer Life and Healthy Ageing" Oct. 22-27, 2001 @http://www.iussp.org/Activities/scc-lon/lon-rep01.php.*

Jagger, Carol. "Health Expectancy Calculation by the Sullivan Method: A Practical Guide" Jun. 13, 2001.*

Jagger, Carol. "Health Expectancy Calculation by the Sullivan Method: A Practical Guide" Jun. 13, 2001. pp. 1-29.*

Smith, V. Kerry. "Longevity Expectations and Death: Can People Predict Their Own Demise?" Sep. 2001. The American Economic Review. vol. 91, Iss. 4. pp. 1126-1134.*

Erfurt, John C. "The Cost-Effectiveness of Worksite Wellness Programs for Hypertension Control, Weight Loss, Smoking Cessation, and Exercise" Spring 1992, vol. 45, Iss. 1. pp. 5-23.*

Hiroyuki Kamata, Kenji Ueshima and Katsuhiko Hiramori, "Home Telecare Life-Style Modification Programs", 20$^{th}$ JCMI (Nov. 2000), pp. 644-645.

* cited by examiner

FIG. 3

| DAILY LIVING HABIT | | | DECISION RESULT | | | | |
|---|---|---|---|---|---|---|---|
| SMOKE | DRINK | EXERCISE | OBESITY+ | HYPER-TENSION+ | HYPER-LIPEMIA+ | HYPER-GLYCEMIA+ | HYPER-URICEMIA+ |
| NO | NO | NO | ⌐\ | ⌐\ | ⌐\ | ⌐\ | ⌐\ | ~27
| NO | NO | A LITTLE | ⌐\ | ⌐\ | ⌐\ | ⌐\ | ⌐\ |
| NO | NO | MUCH | ⌐\ | ⌐\ | ⌐\ | ⌐\ | ⌐\ |
| NO | YES | NO | ⌐\ | ⌐\ | ⌐\ | ⌐\ | ⌐\ |
| NO | YES | A LITTLE | ⌐\ | ⌐\ | ⌐\ | ⌐\ | ⌐\ | ~28
| NO | YES | MUCH | ⌐\ | ⌐\ | ⌐\ | ⌐\ | ⌐\ | ~29
| YES | NO | NO | ⌐\ | ⌐\ | ⌐\ | ⌐\ | ⌐\ | ~30
| YES | NO | A LITTLE | ⌐\ | ⌐\ | ⌐\ | ⌐\ | ⌐\ |
| YES | NO | MUCH | ⌐\ | ⌐\ | ⌐\ | ⌐\ | ⌐\ |
| YES | YES | NO | ⌐\ | ⌐\ | ⌐\ | ⌐\ | ⌐\ |

FIG. 5

Mr. XX:  MALE
DATE OF BIRTH XXXX/YY/ZZ

IF YOU CONTINUE YOUR DAILY LIVING HABIT AS IT IS, IT IS PREDICTED THAT YOUR HEALTHY LIFE EXPECTANCY IS 10 YEARS; AT LEAST DURING THIS PERIOD YOU WILL REMAIN HEALTHY.

~36

HEALTH SCREENING REPORT

Mr. XX:  MALE   DATE OF BIRTH XXXX/YY/ZZ

INQUIRY RESULT
  SUBJECTIVE SYMPTOM, PREVIOUS DISEASE, LIFE-STYLE···

EXAMINATION RESULT
  SOMATOMETRY, BLOOD PRESSURE, URINALYSIS, LIVER FUNCTION TEST···

OVERALL DECISION
  IF YOU CONTINUE YOUR DAILY LIVING HABIT AS IT IS, IT IS PREDICTED THAT YOUR HEALTHY LIFE EXPECTANCY IS 10 YEARS; AT LEAST DURING THIS PERIOD YOU WILL REMAIN HEALTHY.

~37

FIG. 21
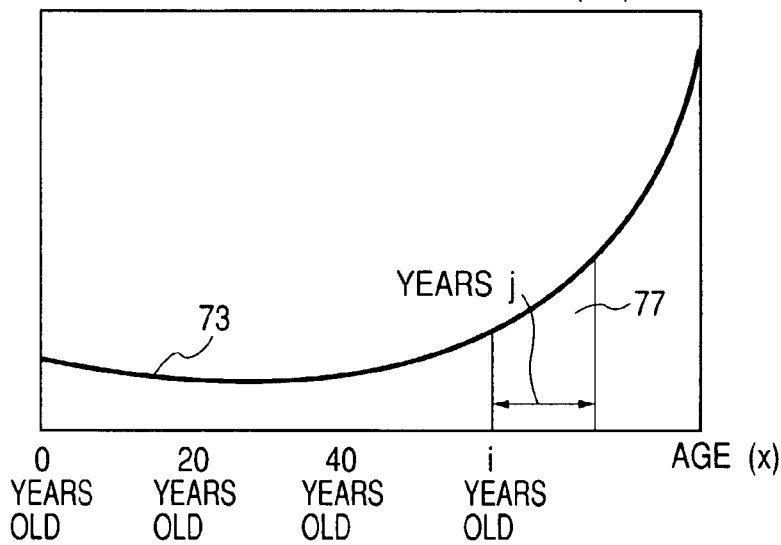
AVERAGE MEDICAL EXPENSES/YEAR (Cx)
$$\text{AGGREGATE MEDICAL PAYMENT (i, j)} = \sum_{x=i}^{i+j-1} Cx$$
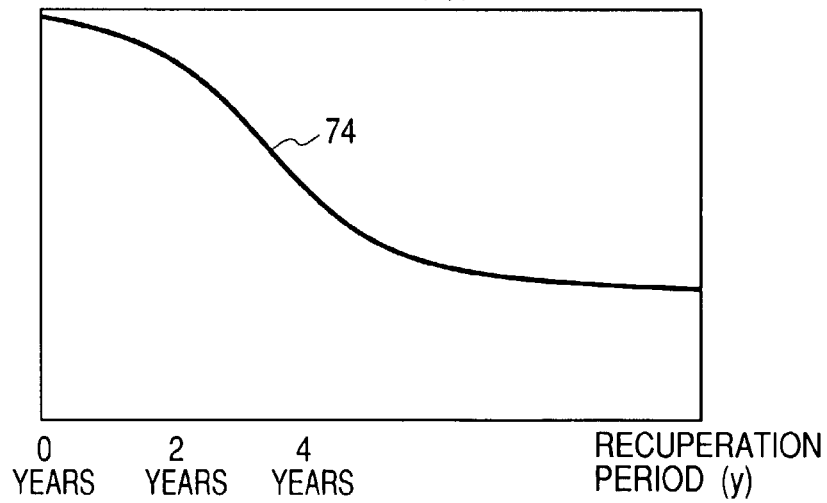
CORRECTION COEFFICIENT (Ay)
$$\text{AGGREGATE MEDICAL PAYMENT (i, j)} = \sum_{x=i}^{i+j-1} Cx \cdot Ax_{-1}$$

FIG. 23
PREDICTED AGGREGATE MEDICAL PAYMENT
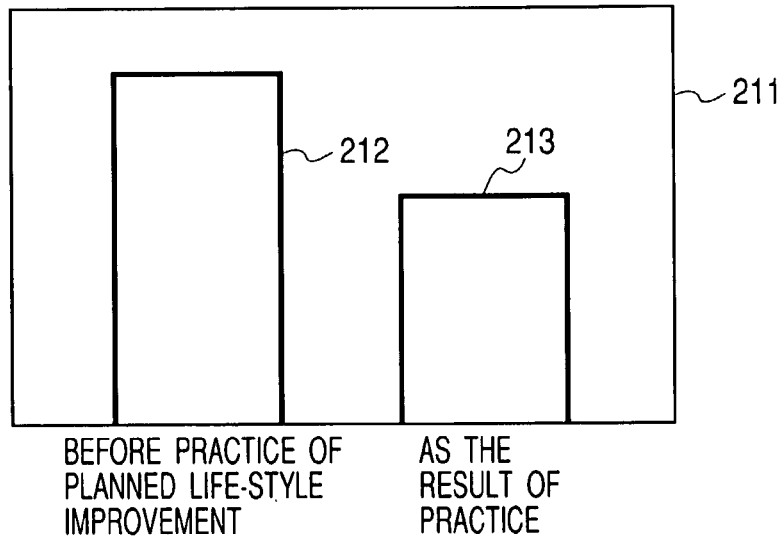
AVERAGE MEDICAL PAYMENT PER YEAR
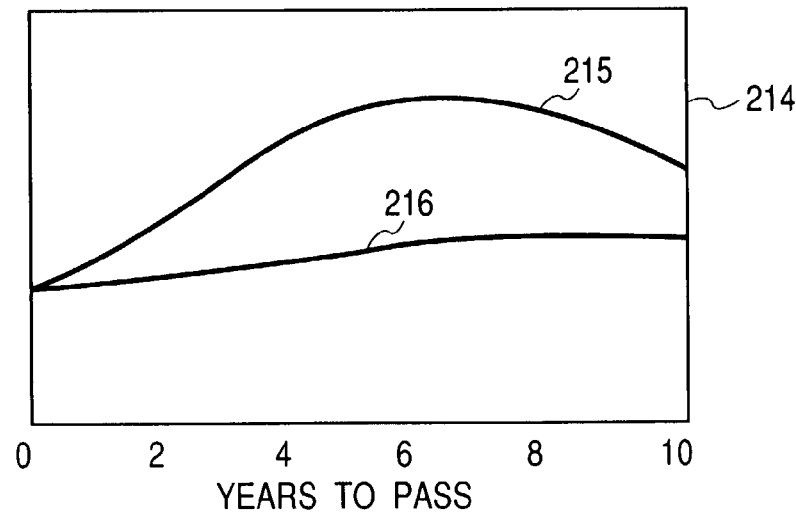
YEARS TO PASS
AVERAGE MEDICAL PAYMENT/YEAR $(k) = \sum_{\text{ALL ASSURED PERSONS}} P(k)$ ~217

HEALTH MANAGEMENT SUPPORT METHOD, SYSTEM AND HEALTHY LIFE EXPECTANCY PREDICTION DATA GENERATION METHOD AND SYSTEM

BACKGROUND OF THE INVENTION

1. Field of the Invention

The present invention relates to a health management support method and system in support of the implementation of health management schemes which are effective for preventing diseases and maintaining health and a method and system for generating healthy life expectancy prediction data.

2. Description of Related Art

To give an example of previous approaches to such health management support, there is a program described in the paper "Program for Supporting Living Habit Improvement Based on the Existing Remote Medical Healthcare Services" (in the collected papers to the 20th Academic Meeting of Medical Informatics Association, pp. 644-645). This paper discusses living habit improvement and guidance services for local inhabitants. The program is intended for rendering health management guidance to its participants for improving their daily living habits such as meals, exercise, and to quit smoking in order to prevent life-style related diseases such as diabetes, hyperlipemia, and hypertension. The service operators guide the participants in their living habits and know how well they follow some advice as guidance by communicating with them through their terminals. The service operators also hold a meeting for group guidance (conducting a workshop on health) to advise the participants on healthcare matters as the guidance for life-style improvement.

In the above previous approach example, comprehensive indexes of personal health conditions are not considered adequately. Therefore, the approach has the following problems: daily health conditions of the participants cannot be grasped quantitatively; there do not exist quantitative indexes of the effects of the particulars of advice as healthcare guidance or a practical method of index calculation does not exist; and it is difficult to make evaluation and optimization based on the particulars of the advice as healthcare guidance.

The above previous approach has another problem. All participants receive guidance, according to the same guidance plan at the workshop on health. However, the guidance about health problems and improvements and the effect thereof would differ for each participant individual. Adequate consideration is not given to a method for developing and providing a life-style improvement plan optimized for each individual of the participants.

The above previous approach has a further problem. Adequate consideration is not given to presenting the information about the effect of practice following life-style improvement guidance to the participants in a form that could boost the participants' will to prevent diseases and pay attention to their own health and life.

SUMMARY OF THE INVENTION

The present invention seeks to solve the foregoing problems of the previous approaches to health management support and its object is to provide such method and system of health management support that are quite effective for preventing diseases and doing self-healthcare. Another object of the invention is to provide a method and system for generating healthy life expectancy prediction data.

To achieve the foregoing objects, in one aspect, the present invention provides a health management support method comprising: a health screening report data entry step which comprises getting health screening report data for each person who underwent health screening; a personal healthy life expectancy prediction data generating step which comprises preparing healthy life expectancy prediction data beforehand as basic data for predicting healthy life expectancy and generating personal healthy life expectancy prediction data from the health screening report data for a person, using the healthy life expectancy prediction data; and a personal healthy life expectancy prediction step which comprises estimating a predicted period of healthy life expectancy of said person, using the generated personal healthy life expectancy prediction data.

In another aspect, the present invention provides a health management support system comprising: a storage unit of healthy life expectancy prediction data in which healthy life expectancy prediction data is stored as basic data for predicting healthy life expectancy; a server unit of health management support that estimates a predicted period of personal healthy life expectancy and generates information about health management, based on the predicted period estimated; and terminal units on which at least the predicted period of healthy life expectancy estimated by the server unit of health management support is displayed.

In yet another aspect, the present invention provides a method for generating healthy life expectancy prediction data comprising: health screening report data collecting steps for collecting a diversity of health screening report data for a plurality of persons who underwent health screening; medical fee bill data collecting steps for collecting medical fee bill data, each of which comprises medical services details and charges for medical services rendered by a medical institution or the like to a person who underwent health screening; medical fee bill data sorting steps for sorting the collected medical fee bill data, according to the results specified in the health screening report data; and a healthy life expectancy prediction data generating step which comprises calculating the percent of the dead and the percent of people who are so sick or disabled as to be difficult to live without help for every age from the sorted medical fee bill data and generating healthy life expectancy prediction data as the basic data for predicting healthy life expectancy, based on the results of the calculation.

In a further aspect, the present invention provides a system for generating healthy life expectancy prediction data comprising: a storage unit of health screening report data in which a diversity of health screening report data for a plurality of persons who underwent health screening is stored; a storage unit of medical fee bill data in which medical fee bill data comprising a diversity of medical services details and charges to a plurality of customers of medical institutions is stored; a healthy life expectancy prediction data generating unit that generates healthy life expectancy prediction data as basic data for predicting healthy life expectancy, using the health screening report data stored in the storage unit of health screening report data and the medical fee bill data stored in the storage unit of medical fee bill data; a storage unit of healthy life expectancy prediction data in which generated healthy life expectancy prediction data is stored.

Other and further objects, features and advantages of the invention will appear more fully from the following description.

BRIEF DESCRIPTION OF THE DRAWINGS

A preferred form of the present invention is illustrated in the accompanying drawings in which:

FIG. 3 shows exemplary healthy life expectancy prediction data;

FIG. 5 shows exemplary printouts of healthy life expectancy information;

FIG. 21 is a graphical representation for explaining exemplary medical payment prediction knowledge data;

FIG. 23 shows exemplary display contents including the predicted amount of aggregate medical payment.

DETAILED DESCRIPTION OF THE PREFERRED EMBODIMENTS

Embodiment 1

With reference to the appended drawings, a preferred Embodiment 1 of the present invention will now be described in detail.

Figure 1:
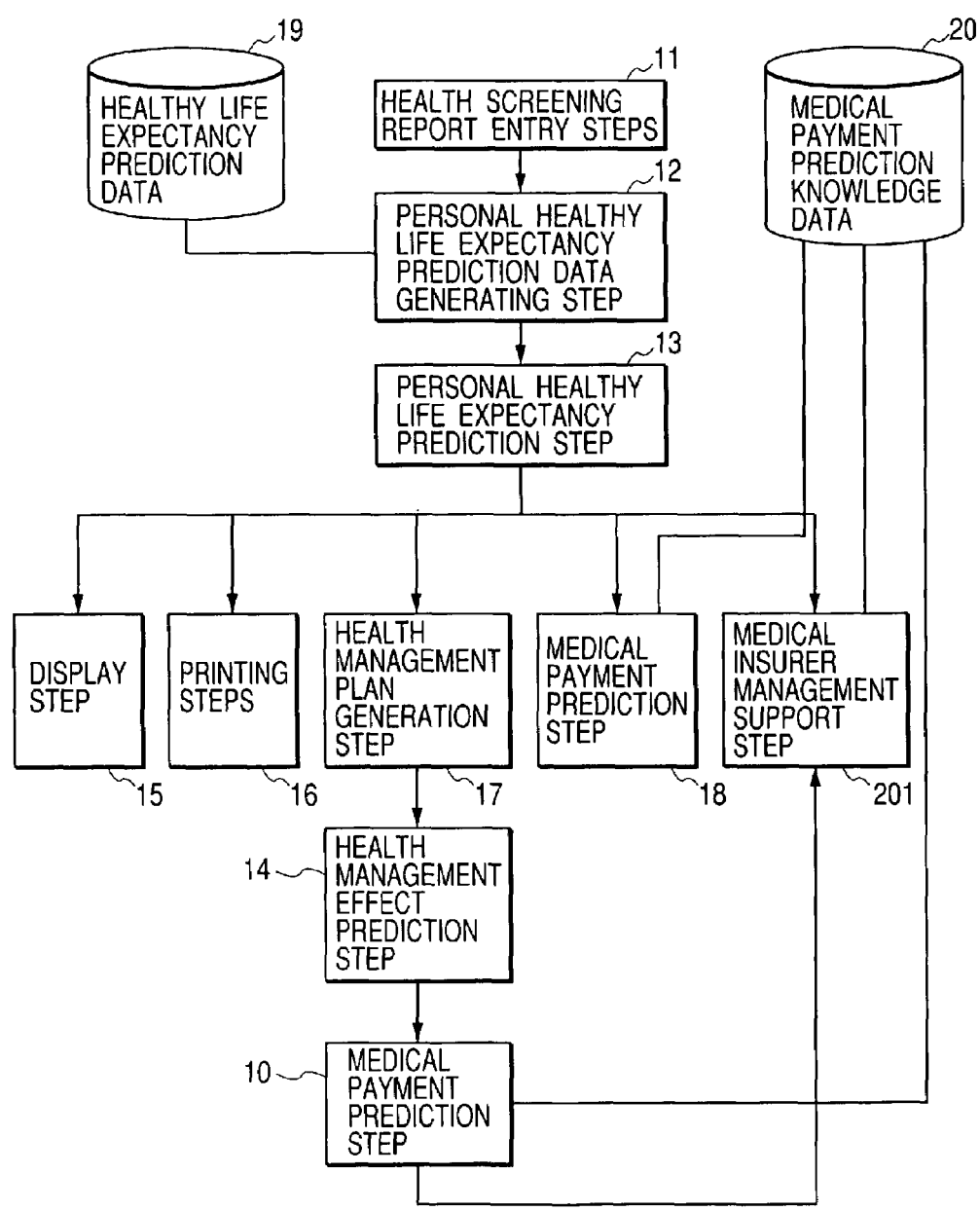
FIG. 1 is a process flow diagram illustrative of the steps of an exemplary method of health management support of the present invention.

FIG. 1 is a process flowchart illustrating an example of the health management support method of the present invention. Reference numeral 11 denotes a health screening report data entry step in which the system to carry out this invention gets report data on each person who underwent health screening. The thus obtained health screening report data is stored in electronic data form in the system. Specifically, getting such data is possible in ways that are exemplified below. The data is downloaded or distributed from health screening institutions, medical insurers, business establishments, data maintenance service providers, etc. that maintain and manage obtained health screening reports in electronic data form to the system via a network or record media. Alternatively, a health screening report printed on paper is scanned by an image scanner, the characters and numeric values described thereon are recognized and transformed into electronic data, and the electronic data is transferred into the system. Alternatively, a keypuncher directly enters the information as described on a health screening report in paper form and the system gets the keyed-in data. The medical insurer means an institution that administrates medical insurance (medical insurer organization). The business establishment means a company or organization at which the person who underwent health screening works.

Reference numeral 12 denotes a personal healthy life expectancy prediction data generating step in which the system generates personal healthy life expectancy prediction data for each person who underwent health screening, using the health screening report data for the person, obtained in the health screening report data entry step. Generating this data is performed by using healthy life expectancy prediction data 19 that is prepared beforehand as the basic data for predicting healthy life expectancy from a diversity of health screening report data. This step will be described in detail later.

Reference numeral 13 denotes a personal healthy life expectancy prediction step in which the system estimates a period of healthy life expectancy for each person who underwent health screening, using the personal healthy life expectancy prediction data generated in the personal healthy life expectancy prediction data generating step. Reference numeral 15 denotes a display step in which the system displays the predicted period of healthy life expectancy and related information, estimated in the personal healthy life expectancy prediction step, on the display screen of a terminal or the like. Before display operation, who orders the display is confirmed so that only the person himself or herself who underwent health screening or a specially authorized operator can see the display content by means of operator authentication with a password, access control, and the like. Reference numeral 16 denotes a printing step in which the system prints out the predicted period of healthy life expectancy and related information, estimated in the personal healthy life expectancy prediction step on paper. The paper on which to print is, for example, a health screening report or a letter sheet or postcard that is posted to each person who underwent health screening, separately from the report.

Reference numeral 17 denotes a health management plan generation step in which the system generates health management plans individually fit for each person who underwent health screening, based on the predicted period of his or her healthy life expectancy estimated in the personal healthy life expectancy prediction step. Reference numeral 18 denotes a medical payment prediction step in which the system calculates predicted medical expenses that the person who underwent health screening may pay in future, based on the predicted period of his or her healthy life expectancy estimated in the personal healthy life expectancy prediction step. Generating this data is performed by using medical payment prediction knowledge data 20 that is prepared beforehand as the basic data for predicting medical payment by considering estimated healthy life expectancy. Reference numeral 201 denotes a medical insurer management support step in which the system predicts the aggregate medical payment of a medical insurer as a whole.

The above steps 15 to 18 and 201 are the processes that are carried out by using the predicted period of healthy life expectancy. From these steps, a necessary step is selected, according to the purpose, and carried out, or a plurality of the steps are carried out concurrently. The following description of Embodiment 1 focuses on estimating personal healthy life expectancy and the steps (15 and 16) for displaying and printing the thus predicted period of healthy life expectancy and related information. Other steps (17, 18, and 201) will be described in detail in other preferred Embodiments.

The health screening report data is the resulting data from health examination, checkup, and the like that are conducted for early detection and treatment. This data comprises, for example, basic information, inquiry results, examination results, and decision results. The basic information is primary information about a fact that a person underwent health screening. The basic information includes the person's name (written in kanji with punctuation characters thereto), sex, date of birth, address, telephone number, place of employment, employee code, medical insurer information (insurer name, insurance card number, etc.), and moreover, the name of the institution that executed the health screening, date of execution, health screening type (periodical medical examination for employees, thorough medical examination, etc.), the personal management number, the doctor in charge, and so on. The inquiry results are information about the health condition of the person who underwent health screening, primarily obtained in the following ways: the person fills out the questionnaire for medical checkup or the doctor asks a patient detailed questions about his or her condition. The inquiry results include previous disease, disease for which the person is undergoing treatment, subjective symptom (palpitation, swelling, liable to get tired, etc.), and daily living habits such as meals (what kinds of food, an intake of calories, whether the person takes regular meals, etc.), exercise (what kind of exercise, how much load or how long, how often, etc.), smoking (whether or not the person smokes, how much the person smokes, how many years the person has smoked, whether the person smoked in the past, period after the person quitted smoking, etc.), drinking (how often the person drinks, what kind of drink, alcohol content, etc.), and job (what job, working hours, when the person comes home, etc.) The examination results are decisions primarily made through examination apparatus or by a doctor whom the person consulted. The examination results include somatometry (height, weight, degree of obesity (such as body-mass index), etc.), eyesight, blood pressure, the pulse, urinalysis, blood test (WBC—white blood cell count, RBC—Red Blood Cell (Erythrocyte) Count, lever function test, lipid metabolism, examination for gout, carbohydrate metabolism, etc.), chest X-ray examination, X-ray examination for the gastrointestinal tract, electrocardiogram, abdominal echography, dental checkup, and so on. The decision results determine whether the person now suffers from a disease or potentially will suffer from a disease in future. The decision results include the decisions for each item of inquiry and examinations from the basic information, inquiry results, and examination results as well as an overall decision by considering everything for a plurality of items.

Then, the personal healthy life expectancy prediction data generating step 12 will be detailed below.

Figure 2:
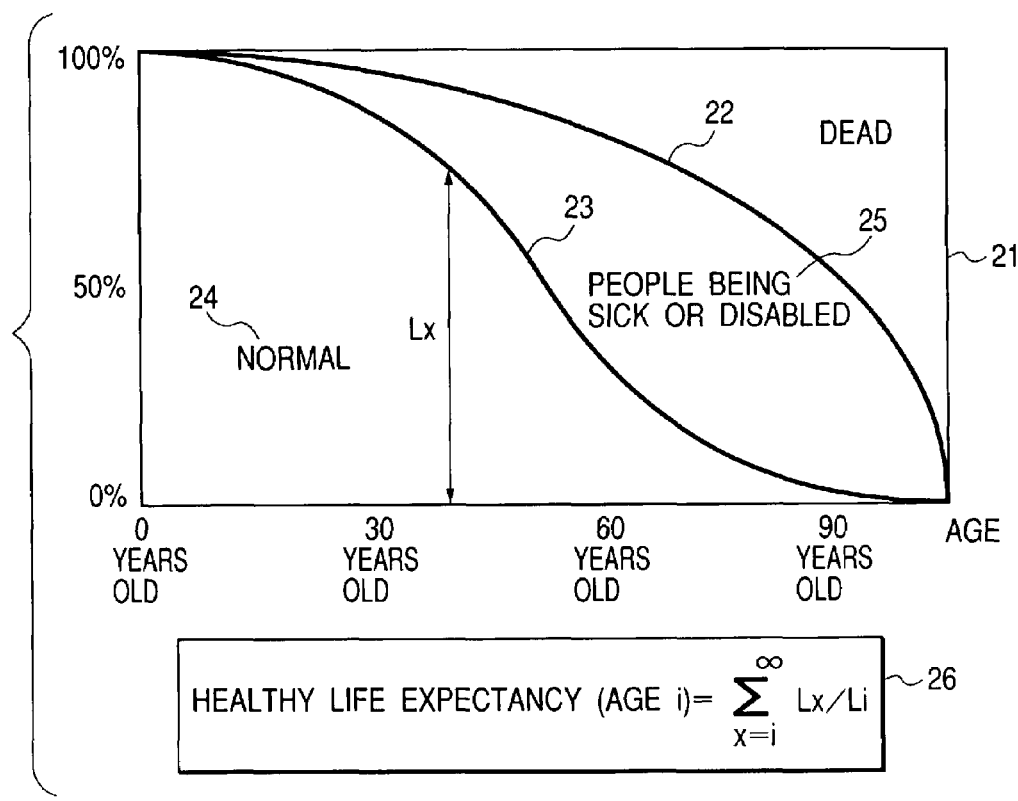
FIG. 2 is a graphical representation for explaining how to estimate a predicted period of healthy life expectance.

FIG. 2 is provided for explaining how to estimate a predicted period of healthy life expectancy. On the graph 21, the transitions of the percent of live people 22 and the percent of normal (healthy) people 23 are plotted, as the age increases along the abscissa; at the age of 0, 100% normal. The normal people means people who survive and live on their own in mind and body in the active state and falls within a domain 24 on the graph below the percent curve of normal people 23. A domain 25 on the graph between the percent curve of survivals 22 and the percent curve of normal people 23 corresponds to the percent of people who need help of someone else, being sick or disabled.

Healthy life expectancy is life expectancy of a person during which the person would be able to live on his or her own in mind and body in the active state. On the graph 21, the life expectancy is an average period from his or her age as of now up to age reaching the percent curve of normal people 23. Specifically, for a person whose age as of now is i, his or her healthy life expectancy is calculated by an equation 26 in FIG. 2; where $L_x$ and $L_i$ are the percents of normal people at age x and i, respectively.

Conventionally, healthy life expectancy has been calculated by using the graph 21 obtained from the average span of human life for the population of the Japanese nation or the population in a specific region, a percentage of the sick, and the like. In this case, the healthy life expectancy thus calculated is only an average thereof for the population of the Japanese nation or the population in a specific region, wherein influence of difference in health condition of individuals on this calculation was not considered at all. In the present invention, using the healthy life expectancy prediction data 19 that is the basic data for predicting healthy life expectancy from a diversity of health screening report data, the system generates healthy life expectancy prediction data on a person-by-person basis from the report data on the health screening that each person underwent. Then, the system predicts healthy life expectancy, taking the health condition difference per person into consideration.

FIG. 3 shows exemplary healthy life expectancy prediction data 19. Graphs 27 in FIG. 3 each represent the transition of the percent of normal people (which corresponds to the curve 23 in FIG. 2) to be used for predicting healthy life expectancy and are prepared for each decision result of health screening. This exemplary data chart contains daily living habit answers about smoking, drinking, and exercise and the graphs whose curve varies, depending on the difference of decision results such as obesity, hypertension, hyperlipemia, hyperglycemia, and hyperuricemia (the graphs will be referred to as healthy life expectancy prediction data differentiated by health screening report data). Specifically, for example, the data from which the percent of survivals and the percent of normal people for each age are obtained is stored in forms such as tables, approximate expressions, and constants and multipliers to be assigned to an equation. The health screening report data differs, depending on whether the person drinks and/or smokes (Yes, No) whether or how much the person does exercise (No, a little, much) and the graphs for the cases of the decision results are shown.

The data given in FIG. 3 is part of the healthy life expectancy prediction data differentiated by health screening report data, stored as the healthy life expectancy prediction data. For health screening report data combinations other than given in FIG. 3, data is prepared. Prediction data also exists for, for example, cases where: the person smokes and drinks as habit and does much exercise usually; none of the above decision results were pointed out to the person; a plurality of decision results such as hypertension and hyperglycemia were pointed out to the person.

Generating personal healthy life expectancy prediction data in the personal healthy life expectancy prediction data generating step 12 is implemented by, for example, selecting prediction data fit for the health screening report data for the person who underwent health screening from the healthy life expectancy prediction data 19 exemplified in FIG. 3. Specifically, for example, suppose that a health screening report for a person who underwent health screening specifies that the person does not smoke, but drinks, and does exercise a little, as the answers to the daily living habit questions, and points out hyperuricemia as a decision result. For this health screening report data, healthy life expectancy prediction data differentiated by health screening report data in a graph 28 in FIG. 3 is selected and output as the healthy life expectancy prediction data for that person.

Using the example of the health management support method of the present invention illustrated in FIG. 1, the procedure of a series of actions of estimating healthy life expectancy for each person who underwent health screening, displaying the information on the estimated healthy life expectancy on the display, and printing that information on paper will be explained below.

First, the system to carry out this invention gets the health screening report data in electronic form for each person who underwent health screening in the health screening report data entry step 11. Then, the system generates healthy life expectancy prediction data for that person from the obtained health screening report data in the personal healthy life expectancy prediction data generating step 12. This step is implemented by, for example, selecting healthy life expectancy prediction data differentiated by health screening report data fit for the health screening report data from the healthy life expectancy prediction data 19 exemplified in FIG. 3.

Then, the system estimates a predicted period of healthy life expectancy of the person, using the healthy life expectancy prediction data generated for the person, in the personal healthy life expectancy prediction step 13. This estimation is performed by applying the equation 26 given in FIG. 2 to the generated healthy life expectancy prediction data. To the above equation, the age of the person must be assigned and this is obtained by, for example, referring to the date of birth included in the basic information of the health screening report data.

Figure 4:
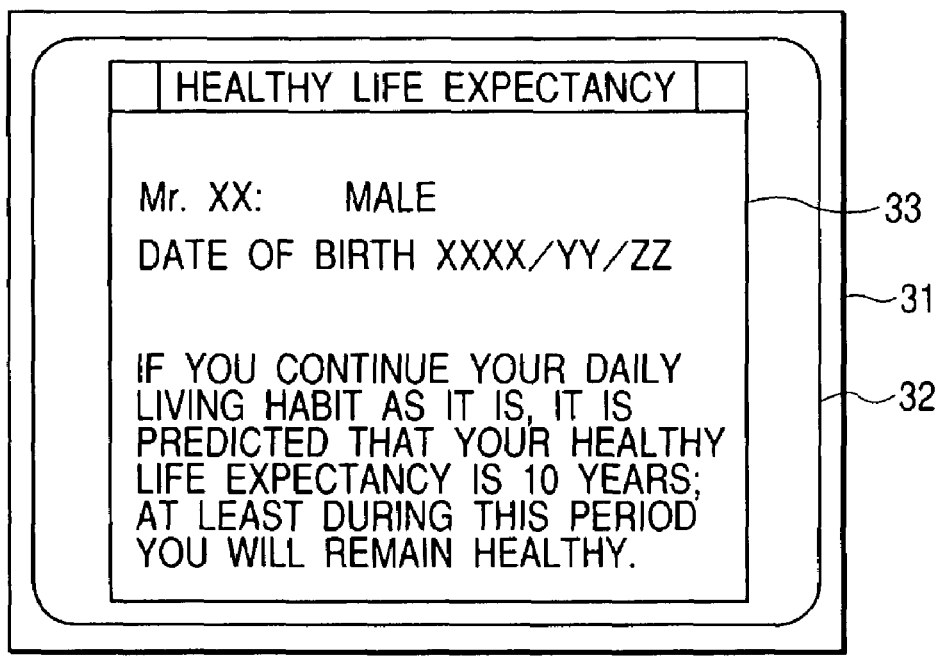
FIG. 4 shows exemplary information for healthy life expectancy displayed on a terminal's display.

Finally, the system displays the predicted period of healthy life expectancy estimated for each person who underwent health screening and related information in the display step 15. FIG. 4 shows exemplary information for healthy life expectancy displayed on a terminal's display. After a person who underwent health screening logs into the system, for example, by entering the user name and password (for user authentication), when the person commands the system to display healthy life expectancy information, the system displays his or her healthy life expectancy and related information in the display window 33 on the screen 32 of the terminal's monitor 31. According to the access control setting, doctors, public health nurses, business establishment's personnel in charge of employee health management, and the like are allowed to display healthy life expectancy information for patients under the care of the doctor, local inhabitants who underwent health screening or employees working at the business establishment if necessary for their duties.

Alternatively, the system prints out the predicted period of healthy life expectancy estimated for each person who underwent health screening and related information on paper in the printing step 16. FIG. 5 shows exemplary printouts of healthy life expectancy information. For example, on a postcard or the like, text like the one in its exemplary form 36 is printed together with the address of a person, so that the postcard can be sent to the person. In order to prevent the third party from reading the printout of the healthy life expectancy information, it is advisable to put a seal to blank the printed text off or enclose the print with a sealed letter and send the letter. The address of the person who underwent health screening is obtained by, for example, referring to his or her address included in the basic information of the health screening report data. Alternatively, as is exemplified by another exemplary form 37 of text in FIG. 5, the healthy life expectancy information is printed on the health screening report to be delivered to the person who underwent health screening after the completion of the processing thereof. As is the case for the display step, user authentication and access control can be applied to the printing step, so that specially authorized operators such as personnel in charge of printing work are exclusively allowed to perform print operation.

According to the above-described health management support method of the present invention, using the healthy life expectancy prediction data that is the basic data for predicting healthy life expectancy from a diversity of health screening report data, the system estimates a predicated period of healthy life expectancy on a person-by-person basis from the report data on the health screening that the person underwent and displays or prints out the predicted period of healthy life expectancy and related information. One noticeable point of the usefulness of the invention is enabling each person who underwent health screening to grasp his or her health condition quantitatively, based on the index of healthy life expectancy, which could boost his or her will to prevent diseases and pay attention to self-healthcare. Another noticeable point of the usefulness of the invention is making it possible to offer an index of health in an intuitively and easily understandable expression, for example, "if you continue your daily living habit as it is, it is predicted that your healthy life expectancy is 10 years; at least during this period you will remain healthy," which is closely related to the daily life of the medically checked individuals, instead of such expression as "smoking causes the rise of the incidence of a lung cancer by 10 times as compared with people who do not smoke" which is reliable information, but hardly intelligible by intuition to the person who underwent health screening as the actual influence of smoking on him or her. Consequently, health management support that is quite effective for disease prevention and healthcare can be provided.

In the above description of Embodiment 1, the healthy life expectancy prediction data differentiated by health screening report data, wherein the prediction data differs, depending on the answers to daily living habit questions asking whether the person does something or whether the person does it a little or much and the decision results appropriate to the person, is prepared as the healthy life expectancy prediction data 19 used in the personal healthy life expectancy prediction data generating step 12. It is also possible to prepare data for numerical information such as years for which the person has smoked and quantity by which the person usually drinks and predict a period of the personal healthy life expectancy, taking this data into account. For example, depending on the factor of the years for which the person has smoked, the transitions of the percent of live people and the percent of normal people are graphically expressed from the data in forms such as tables, approximate expressions, and constants and multipliers to be assigned to an equation. Personal healthy life expectancy prediction data is generated by modifying the healthy life expectancy prediction data differentiated by health screening report data selected, based on the answers to other living habit questions and decision results by the above transitions graph depending on the factor of the years for which the person has smoked. Such modification makes it possible to predict healthy life expectancy with increased accuracy in which numerical information is reflected.

In the above description of Embodiment 1, by way of example, the system predicts healthy life expectancy on a person-by-person basis, using the answers to the daily living habit questions included in the inquiry results and decision results in the health screening report data generated in the personal healthy life expectancy prediction data generating step 12. It is also possible to perform this prediction, using more detailed health screening report data or other information. For example, with regard to smoking, only two data items occurs, Yes and No to the habit question asking whether the person smokes, as exemplified in FIG. 3, but more multiple data items are prepared including quantity that the person smokes everyday, years for which the person has smoked, whether the person smoked in the past, period after the person quitted smoking, etc. Alternatively, healthy life expectancy prediction data differentiated by health screening report data is prepared, based on the difference regarding the sex and occupation included in the basic information and the numerical information such as the degree of obesity and the neutral flat value included in the examination results. In the personal healthy life expectancy prediction data generating step, the system selects healthy life expectancy prediction data differentiated by health screening report data that is fit for the person, taking the above health screening report data items into account. This makes it possible to predict healthy life expectancy with increased accuracy, based on more information.

In the above description of Embodiment 1, by way of example, the healthy life expectancy prediction data 19 used in the personal healthy life expectancy prediction data generating step 12 is stored such that different graphs of prediction data are generated and stored for different results of health screening report data. It is also possible to generate and store this data in another manner. This manner is described below. For example, a reference graph (for the data expressed in a table, equation, etc.) is prepared and a step is added in which variation factors (multipliers or constants to the graph) for processing such as modification and interpolation to the graph are generated and stored. Generating healthy life expectancy prediction data on a person-by-person basis is implemented by selecting modification factors determined, according to the health screening report data for the person, and executing the processing using the modification factors to the reference graph. It is also possible to prepare a plurality of reference graphs and use a suitable one accordingly or combine this manner with the method illustrated in FIG. 3. A quite a great number of variants of healthy life expectancy prediction data differentiated by health screening report data is required if prediction is executed by taking minor difference in health screening report data into account. In that event, it is advisable to use the above manner, thereby making it possible to generate and store such data efficiently.

In the above description of Embodiment 1, by way of example, the healthy life expectancy prediction data 19 used in the personal healthy life expectancy prediction data generating step 12 is stored such that different graphs of prediction data are generated and stored for different results of health screening report data. It is also possible to share a single graph of healthy life expectancy prediction data if variation by different results of health screening report data is negligibly small or prediction data for one person is virtually the same as the health screening report data for another person. Reduced data storage space and faster processing are achievable.

In the above description of Embodiment 1, from the health screening report data for each person who underwent health screening obtained in the health screening report data entry step, the system generates healthy life expectancy prediction data for that person in the personal healthy life expectancy prediction data generating step 12. When generating this data, it is also possible to modify, if necessary, the health screening report data obtained in the health screening report data entry step. For example, if the examination method, normal range, units of values representing the results of examination, and the like for the results of examination executed at a particular health screening institution differ from those represented in the healthy life expectancy prediction data obtained at another examination institution, a step is added in which data modification is performed, according to a transformation procedure prepared beforehand. Alternatively, if a different form of questionnaire for medical checkup is used and the answer to a question is not found in the standard inquiry results, a step is added in which the answer is reflected in similar inquiry result data. Such modification can automatically be made by using the information about the institution that executed the health screening included in the basic information or adding necessary information (units, questions, etc.) to the inquiry results and the examination results. This modification makes it possible to correctly generate personal healthy life expectancy prediction data even if health screening reports and contents from different health screening institutions are somewhat different and estimate a predicted period of healthy life expectancy with increased accuracy.

In the above description of Embodiment 1, the personal healthy life expectancy prediction data generating step 12 is carried out by selecting healthy life expectancy prediction data differentiated by health screening report data that is fit for the health screening report data for the person who underwent health screening from the healthy life expectancy prediction data 19. It is also possible to select a plurality of healthy life expectancy prediction data differentiated by health screening report data, based on which the healthy life expectancy prediction data for the person is generated. In some case, personal health screening report data is not consistent with the classification of health screening report data in the previously prepared healthy life expectancy prediction data, because, for example, the health screening items are different by reason of the health screening institution or the person who underwent health screening, or due to missing items of health screening report data because of failure to answer questions in the questionnaire for medical checkup or examination was not performed for the items. In such case, steps are added in which the system selects a plurality of possible healthy life expectancy prediction data differentiated by health screening report data from the health screening report data for the person who underwent health screening and the selected data is processed by suitable modification (for example, averaging or the like), thus generating the healthy life expectancy prediction data for the person. For example, if the answer to the daily living habit question about exercise is missing, all items other than the exercise (for example, three items 28, 29, and 30 in the chart with the graphs illustrated in FIG. 3) are selected and modified. When displaying and printing out the healthy life expectancy information in the display step and the printing step, it is also possible to display and printout supplementary information that such modification was made if necessary. Even if the health screening items are different or some items are missing in the health screening report, the above modification processing makes it possible to estimate a predicted period of healthy life expectancy, while holding the accuracy decrease to a small degree by the maximum use of the acquired health screening report data.

In the above description of Embodiment 1, as the healthy life expectancy prediction data 19, graphs representing the transitions of the percent of normal people differentiated by health screening report data are generated and stored. It is also possible to generate and store graphs representing the transitions of the percent of live people (the curve 22 in the graph shown in FIG. 2). A step is added in which average life expectancy is calculated by using the percent of survivals, so that the average life expectancy can be displayed and printed together with the healthy life expectancy period in the display step and the printing step. Furthermore, a step is added in which duration of disease and/or disability (the period of the life state being sick or disabled) is calculated by subtracting the healthy life expectancy period from the average life expectancy, so that the information thereof can also be displayed and printed as well as the average life expectancy. Thus, the system can present more intelligible information for healthcare to each person who underwent health screening, which could further boost his or her will to prevent diseases and pay attention to self-healthcare.

In the above description of Embodiment 1, the system estimates a predicted period of healthy life expectancy of each person who underwent health screening in the personal healthy life expectancy prediction step 13. It is also possible to estimate age of the person at which his or her healthy life expectancy period terminates as well as his or her life expectancy period. For example, a step is provided in which, to the healthy life expectancy period, his or her age calculated from the date of birth of the person included in the basic information of the health screening report data is added. Consequently, the estimated age of the person at which his or her healthy life expectancy period terminates can be displayed and printed together with the healthy life expectancy period in the display step and the printing step. Thus, the system can present more intelligible information for healthcare to each person who underwent health screening, which could further boost his or her will to prevent diseases and pay attention to self-healthcare.

Embodiment 2

Next, a preferred Embodiment 2 of the present invention will be described in detail, with reference to the appended drawings.

Embodiment 2 concerns the health management plan generation step 17 mentioned in FIG. 1. In the health management plan generation step 17, the system generates health management plans individually fit for each person who underwent health screening, based on the predicted period of his or her healthy life expectancy estimated in the personal healthy life expectancy prediction step. In Embodiment 2, an illustrative implementation example of the health management plan generation step will be explained, comprising health screening plan generation steps for generating health screening recommendation plans for each medically checked person and healthy life-style plan generation steps for generating practice recommendation plans for guiding each person in improving his or her living habits such as meals, exercise, and smoking.

Figure 6:
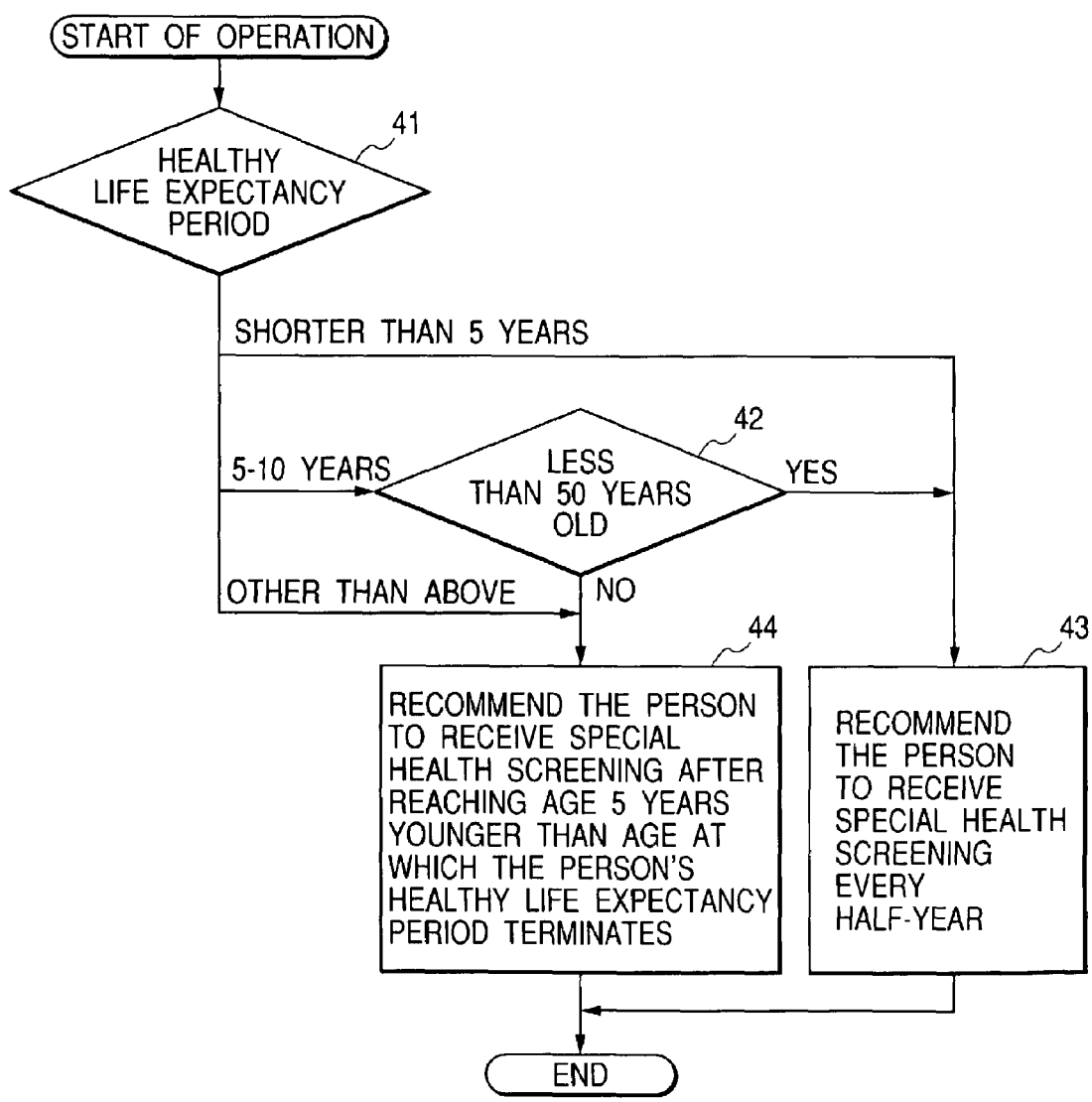
FIG. 6 illustrates an exemplary procedure of health screening plan generation steps included in the present invention.

FIG. 6 illustrates an exemplary procedure of the health screening plan generation steps included in the present invention. Based on the predicted period of the healthy life expectancy of a person who underwent health screening, the system to carry out this invention determines when the person should receive health screening (intervals, frequency, etc.) in future and what kind of health screening he or she should receive. The system determines what year range within which the predicted healthy life expectancy period falls; for example (1) shorter than five years; (2) five to ten years; or (3) other than the above (that is, ten years and over) (step 41 in FIG. 6). If the period is shorter than five years, the system judges the probability high that the person will become sick or disabled in near future and generates a plan to recommend the person to additionally receive special health screening every half year besides normal health screening (step 43 in FIG. 6). If the healthy life expectancy period is ten years and over, the system judges that probability that the person will become sick or disabled in near future is not high and generates a plan to recommend the person to additionally receive special health screening only after the person will reach age five years younger than his or her age at which the healthy life expectancy period terminates (step 44 in FIG. 6).

If the person's healthy life expectancy period falls within the range of five to ten years, the system again checks the age of the person (step 42 in FIG. 6). If the person's age is less than 50 years old, the system judges that early guidance should be required for the person and generates a plan to recommend the person to receive additional health screening as in the case that the healthy life expectancy period is shorter than five years (step 43 in FIG. 6). If the person's age is not less than 50 years old, the system generates a plan to recommend the person to receive additional health screening as in the case that the healthy life expectancy period is ten years and over (step 44 in FIG. 6).

Figure 7:
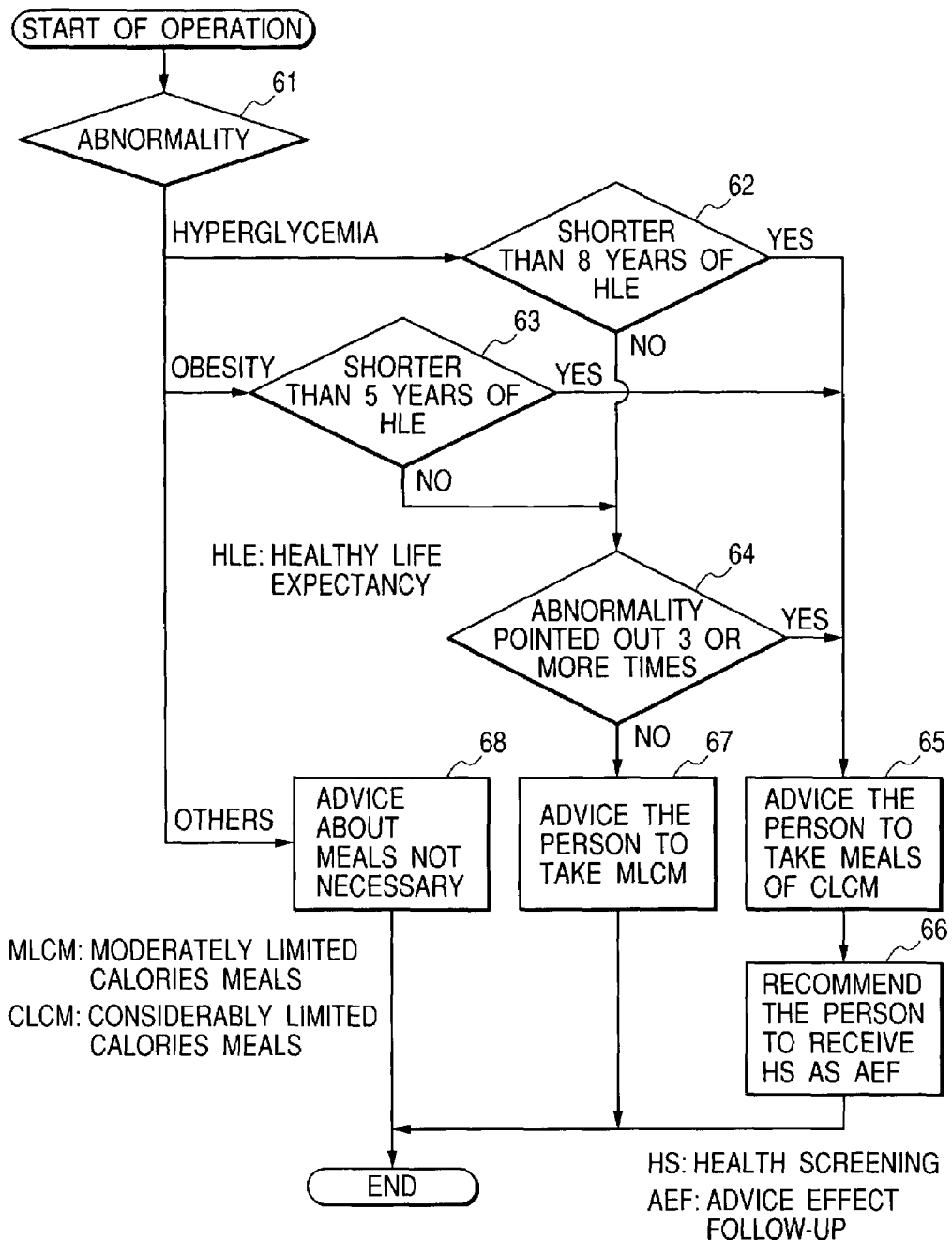
FIG. 7 illustrates an exemplary procedure of healthy life-style plan generation steps included in the present invention.

FIG. 7 illustrates an exemplary procedure of the healthy life-style plan generation steps included in the present invention. Based on the predicted period of the healthy life expectancy of a person who underwent health screening, the system to carry out this invention determines whether advice about meals is required for the person in future and what advice to be given. The system judges abnormality pointed out as a decision result included in the health screening report data to be (1) hyperglycemia; (2) obesity; or (3) others (including neither hyperglycemia nor obesity) (step 61 in FIG. 7). If the abnormality is hyperglycemia and the healthy life expectancy period is shorter than eight years (step 62 in FIG. 7) or if the abnormality is obesity and the healthy life expectancy period is shorter than five years (step 63 in FIG. 7), the system generates a plan to advise the person to take considerably limited calories meals (step 65 in FIG. 7). If the decision results of the health screening report data include neither hyperglycemia nor obesity, the system regards the advice about meals as unnecessary and does not generate any plan (step 68 in FIG. 7).

If the healthy life expectancy period is neither shorter than eight years (with hyperglycemia) nor shorter that five years (with obesity), the system judges by the past health screening report data for the person who underwent health screening (step 64 in FIG. 7). Unless the same abnormality was pointed out and some advice about meals was given three or more times in the past, the system generates a plan to advise the person to take moderately limited calories meals (step 67 in FIG. 7). If the past advice about meals and its effect are judged insufficient, the system generates a plan to advise the person to take considerably limited calories meals (step 65 in FIG. 7).

Having generated a plan to advise the person to take considerably limited calories meals, the system recommends the person to receive additional health screening in order to pursue the effect of the advice continuously and in detail (step 66 in FIG. 7). In this health screening, the patient (the advised person) is checked up for abnormality, for example, hyperglycemia and/or obesity.

For the person who underwent health screening and to whom both hyperglycemia and obesity were pointed out as decision results in his or her health screening report data, the system generates a plan for meals, according to the hyperglycemia result. In this case, the plan for meals may be modified by, for example, adding a new advice that is stricter.

The thus generated health management plans such as health screening recommendation plans and plans as guidance for lifestyle-related diseases prevention are displayed in the display step and printed in the printing step as is the case for healthy life expectancy on a person-by-person basis.

Figure 8:
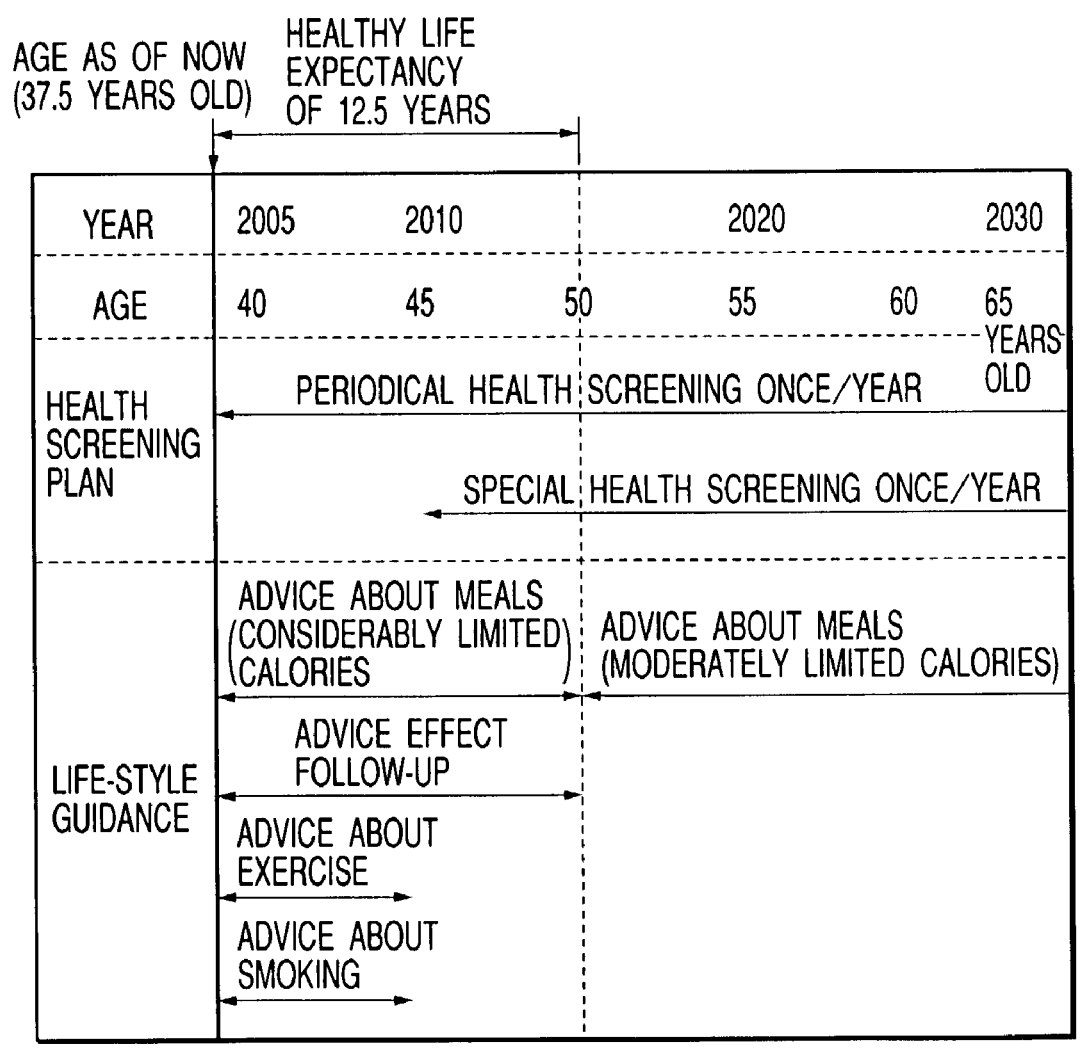
FIG. 8 represents an exemplary health management plan displayed, fit for a person who underwent health screening.

FIG. 8 represents an exemplary health management plan, fit for the person who underwent health screening, displayed after generated in the health management plan generation step. This exemplary plan is a health management plan generated, according to the health screening plan generation steps and the healthy life-style plan generation steps, based on the predicted period of the person's healthy life expectancy estimated in the personal healthy life expectancy prediction step. In this example, it is assumed that the age of the person is 37.5 years old, the predicted period of the person's healthy life expectancy estimated in the personal healthy life expectancy prediction step is 12.5 years, and obesity is pointed out as a decision result of the health screening report data (the past health screening reports pointed out obesity three times).

Because the person's healthy life expectancy period is 10 years and over, in the health screening plan generation steps, the system generates a plan to recommend the person to additionally receive special health screening only after the person will become 45 years old, five years younger than his or her age at which the healthy life expectancy period terminates, besides periodical health screening that is currently executed. Because obesity is pointed out and was done three times in the past, in the healthy life-style plan generation steps, the system generates a plan to advise the person to take considerably limited calories meals and a plant to recommend the person to receive health screening for pursuing the effect of the advice (advice effect follow-up) . According to the plan, the period of practice following the advice about meals will terminate at the age (50 years old) at which the person's healthy expectancy period terminates. For years after that age, a plan to advise the person to take moderately limited calories meals has been generated.

In this example, the advice effect follow-up is performed for obesity on the supposition that the person measures his or her weight or percent of body fat by himself or herself. If it is required that a follow-up check be performed at a health screening institution, it is advisable to schedule the follow-up check in agreement with the health screening schedule and planned checkup generated in the health screening plan generation steps if necessary.

In this example, according to the same procedure as for the advice about meals, plans for advice about exercise and smoking which are other living habits are also generated.

As described above, the health management support method of the present invention includes the health management plan generation step in which the system generates health management plans individually fit for each person who underwent health screening, based on the predicted period of his or her healthy life expectancy estimated in the personal healthy life expectancy prediction step. A noticeable point of the benefit hereof is making it possible to advise each individual person who underwent healthy screening to do daily practice optimized for the person and efficiently implement health management support that is quite effective for preventing diseases and doing self-healthcare.

In the health management support method of the present invention, health management plans are generated, based on not only the predicted period of healthy life expectancy of the medically checked person, but also other information, such as the age of the person, abnormality pointed out as a decision result, and the decision results in the past health screening reports, which are combined with the predicted healthy life expectancy. Thus, the method also has advantage of making it possible to generate plans that are more suitable for each person who underwent health screening.

In Embodiment 2 of the health management plan generation step, health screening recommendation plans and plans as guidance for lifestyle-related diseases prevention are generated by following the procedures shown in FIGS. 6 and 7. However, these procedures should not be considered as fixed. The generation steps and numeric values (for example, the period of healthy life expectance used in decision) can be changed if other factors and new views are obtained. Alternatively, a step may be provided in which, after health management plans generated in the health management plan generation step, as exemplified in FIG. 8 are displayed in the display step 15, experts such as public health nurses can interactively modify the health management plans on the display. Alternatively, a step may be provided in which, after health management plans are printed out in the printing procedure, experts can revise the plans, referring to the printed text of the plans, thus generating the revised health management plans. Referring to the healthy life expectancy and related information generated in the health management plan generation step, experts can modify the information with their view, so that health management plans that are more suitable for each person who underwent health screening can be generated.

Embodiment 3

Next, a preferred Embodiment 3 of the present invention will be described in detail, with reference to the appended drawings.

Embodiment 3 concerns the medical payment prediction step 18 included in FIG. 1. The medical payment prediction step 18 is the step in which the system calculates predicated medical expenses that the person who underwent health screening may pay in future, based on the predicted period of his or her healthy life expectancy estimated in the personal healthy life expectancy prediction step. Generating this data is performed by using medical payment prediction knowledge data 20 that is prepared beforehand as the basic data for predicting medical payment by considering estimated healthy life expectancy.

FIG. 21 is provided for explaining exemplary medical payment prediction knowledge data. A first graph 73 represents the transition of average medical expenses a year Cx per person who underwent health screening depending on age x. In general, medical payment greatly varies, depending on the ages. Medical payment prediction knowledge data describing such transition is stored in forms such as tables, approximate expressions, and constants and multipliers to be assigned to an equation. Such prediction knowledge data is generated by using, for example, "national medical expenses," the result of national survey about medical expenses performed by the Statistics and Information Department, Minister's Secretariat, Ministry of Health, Labour and Welfare or by independently collecting statistics on medical expenditures.

Figure 10:
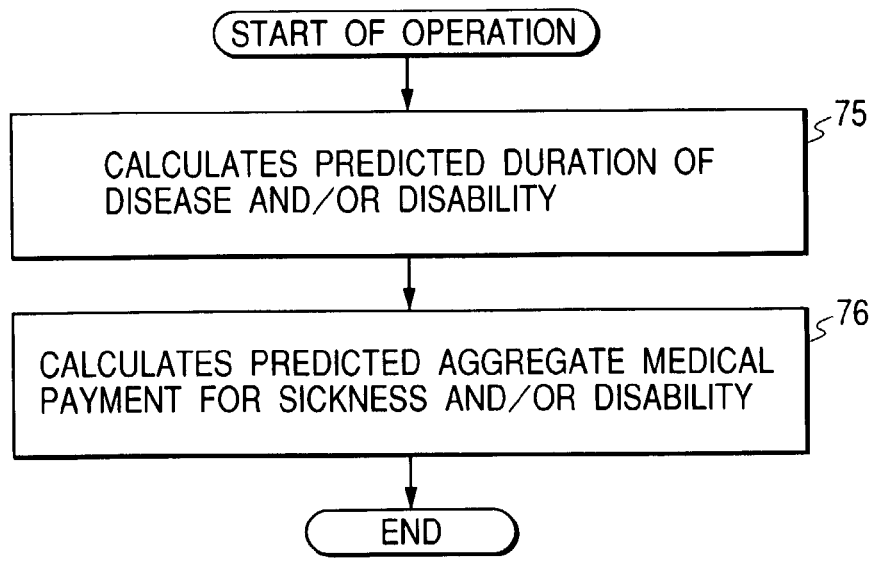
FIG. 10 illustrates an exemplary procedure of a medical payment prediction step included in the present invention.

FIG. 10 illustrates an exemplary procedure of the medical payment prediction step included in the present invention. Using FIG. 10, a procedure of estimating medical expenses will be explained below.

For each person who underwent health screening, the system first calculates predicated duration of disease and/or disability (the period of the life state being sick or disabled), based on the predicted period of his or her healthy life expectancy estimated in the personal healthy life expectancy prediction step (step 75 in FIG. 10). This period is obtained by subtracting the predicted period of the person's healthy life expectancy from average life expectancy. The average life expectancy obtained, based on the national survey result is used. Alternatively, the average life expectancy is used, obtained by generating and storing data describing the transitions of the percent of live people as the healthy life expectancy prediction data 19 and calculating the average life expectancy for the individual person, using such transition data in the additional step as described in Embodiment 1.

Then, the system calculates the aggregate medical payment predicted for the sickness and/or disability (step 76 in FIG. 10). The predicted aggregate medical payment is the summation of average medical expenses a year for the predicated duration (j years) of disease and/or disability starting from the age (i years old) at which the predicted healthy life expectancy terminates, which corresponds to a domain 77 in FIG. 21. Specifically, the predicted aggregate medical payment is calculated by an equation 78 given in FIG. 21.

The predicted aggregate medical payment thus calculated is displayed in the display step and printed in the printing step in the same was as for the healthy life expectancy on a person-by-person basis.

As described above, the health management support method of the present invention includes the medical payment prediction step in which the system calculates predicted medical expenses that the person who underwent health screening may pay in future, based on the predicted period of his or her healthy life expectancy estimated in the personal healthy life expectancy prediction step. A noticeable point of the benefit hereof is that the health condition of the person who underwent health screening can be represented by the index of medical payment that greatly influences the future life design of the person, thus making it possible to implement health management support that is quite effective for preventing diseases and doing self-health-care.

In the above description of Embodiment 3, in the medical payment prediction step, the system calculates the predicted aggregate medical payment by using the period of healthy life expectancy and the duration of disease and/or disability predicted for the person. It is also possible to add other information influencing medical payment to the medical payment prediction knowledge data and use that information in the calculation in the medical payment prediction step. For example, the calculation can be executed, taking the influence of how long the person's recuperation period is on the medical payment into account. A second graph 74 in FIG. 21 represents the transition of average medical expenses a year influenced by the person's recuperation period, using correction coefficient Ay. In this example of graph representation, the average medical expenses a year decrease by the correction coefficient as the recuperation period is prolonged. Data from which this graph is plotted is stored in forms such as tables, approximate expressions and constants and multipliers to be assigned to an equation as additional medical payment prediction knowledge data.

In the medical payment prediction step, the system calculates predicted medical expenses by using this correction coefficient. Specifically, the average medical expenses a year per age are multiplied by the correction coefficient depending on the recuperation period and the summation thereof is calculated. This is implemented by using an equation 79 given in FIG. 21 instead of the equation 78. The calculation can be executed by using diverse information that influences medical payment so that medical payment can be predicted with increased accuracy.

Embodiment 4

Next, a preferred Embodiment 4 of the present invention will be described in detail, with reference to the appended drawings.

In Embodiment 2, the health management plan generation step was explained, wherein the system to carry out this invention generates health management plans individually fit for each person who underwent health screening. Embodiment 4 concerns a health management effect prediction step in which the system estimates change to the predicted period of healthy life expectancy of a person, the change expected, assuming that the person would practice life-style improvement advised in a health management plan generated in the health management plan generation step.

Figure 9:
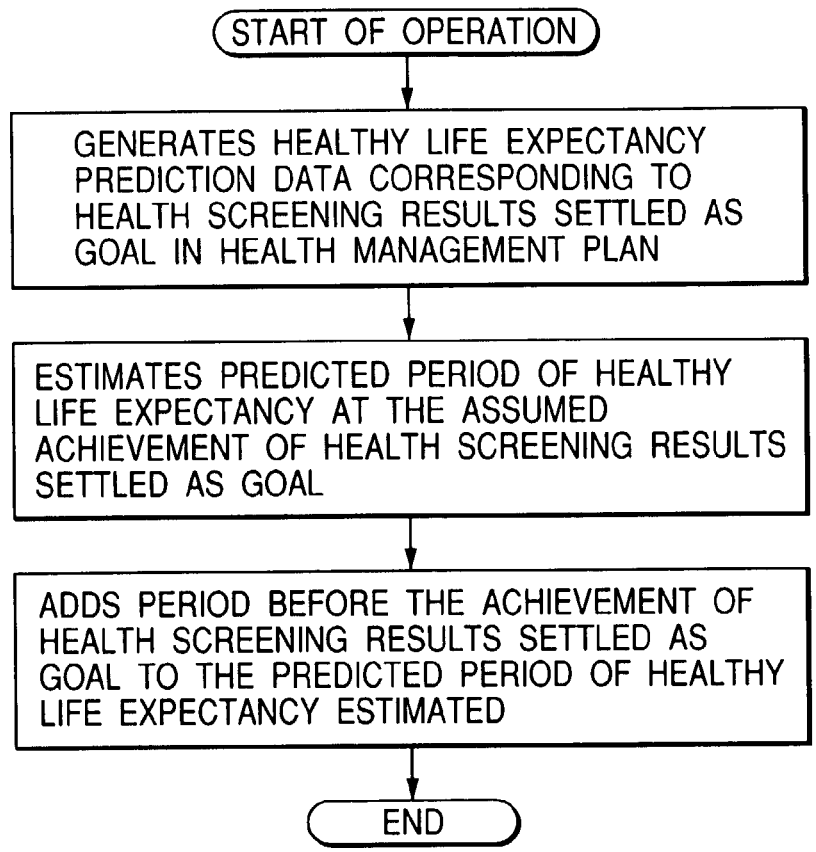
FIG. 9 illustrates an exemplary procedure of a health management effect prediction step included in the present invention.

FIG. 9 illustrates an exemplary procedure of the health management effect prediction step included in the present invention. First, the system generates healthy life expectancy prediction data corresponding to the health screening results settled as the goal in the health management plan. For example, if obesity is pointed out as a decision result of the health screening report data, the goal of the health management plan is getting rid of the ill-health pointed out. In this procedure, the system generates healthy life expectancy prediction data that would apply if the person should attain the goal. Specifically, by following the same procedure as for the personal healthy life expectancy prediction data generating step 12 described in Embodiment 1, the system selects prediction data corresponding to the health screening results that would apply if the person should attain the goal from the healthy life expectancy prediction data differentiated by health screening report data stored as the healthy life expectancy prediction data.

Then, the system estimates a period of healthy life expectancy predicted at the assumed achievement of the health screening results settled as the goal, using the selected prediction data. Specifically, this can be implemented by following the same procedure as for the personal healthy life expectancy prediction step 13 described in Embodiment 1. However, the system estimates the above period, using the age at the assumed achievement of the health screening results, instead of the age as of now of the person who underwent health screening.

Finally, the system adds the period before the achievement of the health screening results settled as the goal to the predicted period of healthy life expectancy estimated. The resultant period is healthy life expectancy expected, assuming that the person would practice life-style improvement advised in the health management plan.

The predicted period of healthy life expectancy thus estimated and related information are displayed in the display step and printed in the printing step as is the case for healthy life expectancy on a person-by-person basis.

Figure 11:
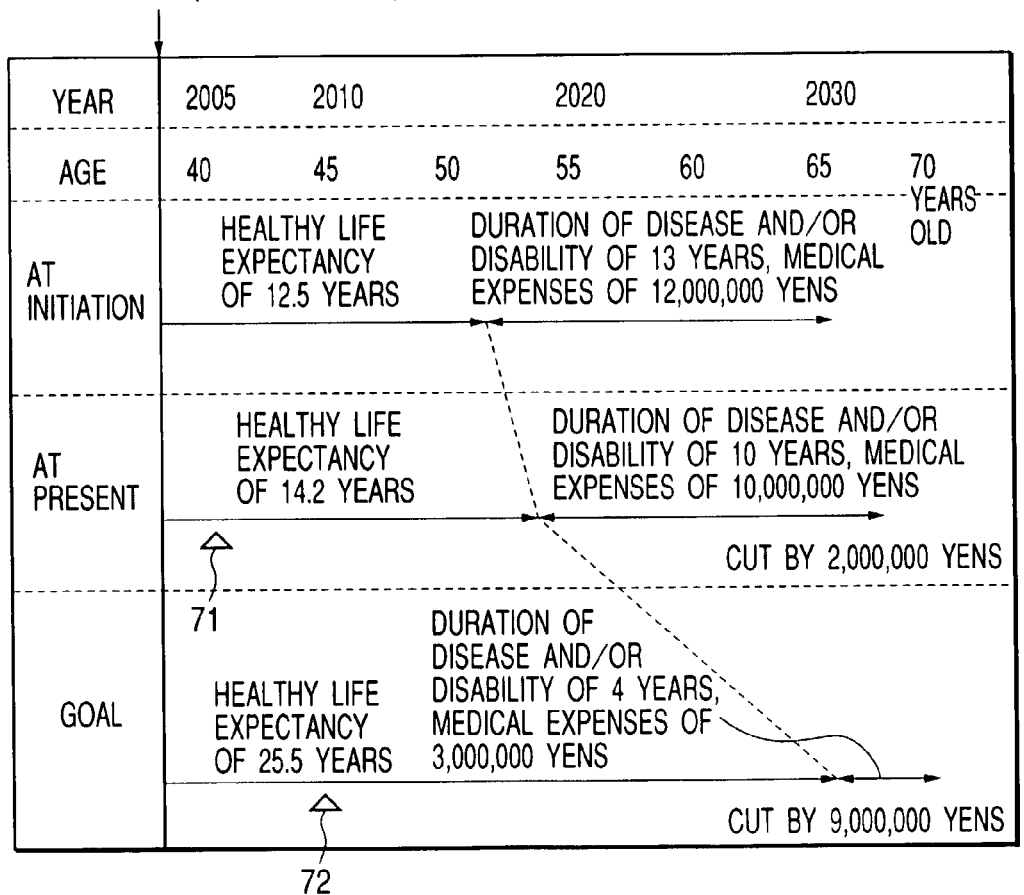
FIG. 11 shows exemplary displayed information about change to the predicted period of healthy life expectancy.

FIG. 11 shows exemplary displayed information about change to the predicted period of healthy life expectancy calculated in the health management effect prediction step. This display example is provided on the following assumption: a person underwent health screening when he or she was 37.5 years old, it is judged that life-style improvement is necessary, and the person is practicing the life-style improvement advised in the health management plan generated in the health management plan generation step. At the start of the practice according to the health management plan, the person's healthy life expectancy is 12.5 years, which corresponds to the predicted period estimated in the personal healthy life expectancy prediction step 13 described in Embodiment 1. His or her healthy life expectancy at the assumed achievement of the goal of the health management plan is 25.5 years, which is estimated in the above described procedure of Embodiment 4. Marking 72 in FIG. 11 indicates when the person will attain the goal and have gotten rid of the ill-health problem pointed out in the health screening report data.

As described above, the health management support method of the present invention makes it possible to predict change of healthy life expectancy expected by the practice according to the health management plan by using the health management effect prediction step. One noticeable point of the benefit hereof is making it possible to quantitatively evaluate the effect of the guidance for lifestyle-related diseases prevention such as advice about meals and advice about exercise with the index of healthy life expectancy and present the evaluation to each person under the guidance and experts such as public health nurses, and thus evaluate and optimize personal health condition and related matters, based on the health management plan. Another noticeable point of the benefit is making it possible to make quantitative presentation of the effect of practice following the guidance for lifestyle-related diseases prevention and boost and keep the participants' will to prevent diseases and do self-healthcare.

While the exemplary procedure of the health management effect prediction step illustrated in FIG. 9 is applied in the above description of Embodiment 4, another procedure can be used for predicting healthy life expectancy expected as the result of life-style improvement. For example, while the system estimates a period of healthy life expectancy predicted at the assumed achievement of health screening results settled as the goal and adds the period before the achievement of health screening results settled as the goal to the above predicted period in the procedure illustrated FIG. 9, it is also possible that the system estimates the above period predicted at the present time and outputs the thus estimated period as the healthy life expectancy expected as the result of life-style improvement. Alternatively, if the system cannot exactly estimate the healthy life expectancy expected as the result of life-style improvement due to errors and deficiency of healthy life expectancy prediction data differentiated by health screening report data, it is also possible that the system selects one of multiple estimation methods thereof or uses a combination of methods and makes appropriate correction. Using such procedure, the system can estimate the healthy life expectancy expected as the result of life-style improvement with increased accuracy.

While healthy life expectancy expected as the result of practice according to the health management plan is estimated by the health management effect prediction step in the above description of Embodiment 4, it is also possible to add a step in which healthy life expectancy during the above practice is estimated. For example, assume that a person receives the next health screening one year after he or she starts the above practice. From the health screening report data obtained by this health screening, the system estimates a predicted period of his or her healthy life expectancy. The thus estimated period includes, for example, the time elapsed after the start of the practice, and this is displayed. An example hereof is shown in the row "at present" in FIG. 11. In this example, healthy life expectancy of 14.2 years is shown; that is, the assumed healthy life expectancy of 13.2 years predicted from the health screening report data plus one year that has passed after the start. Marking 71 in FIG. 11 indicates the present time, one year after the start of the practice according to the health management plan. This display manner enables each person under improvement guidance and experts to grasp the effect of the practice following the guidance for lifestyle-related diseases prevention with the time passage information and makes it possible to further boost and keep the person's will to prevent diseases and do self-healthcare. Such display manner also enables the following. If the effect of the guidance for lifestyle-related diseases prevention to a small degree is found, further improvement and measures such as re-planning the guidance are taken at an early stage.

Embodiment 5

Next, a preferred Embodiment 5 of the present invention will be described in detail, with reference to the appended drawings.

In Embodiment 4, the procedure of the health management effect prediction step by which the system estimates a predicted period of healthy life expectancy expected, assuming that the person would practice the life-style improvement advised in the health management plan was explained. Embodiment 5 concerns a medical payment prediction step in which the system calculates predicted medical payment change, based on the predicted period estimated in Embodiment 4.

Predicted medical payment change is calculated by estimating medical expenses that the person who underwent health screening may pay in future, based on the predicted period of his or her healthy life expectancy estimated in the health management effect prediction step. The procedure thereof is the same as the procedure of the medical payment prediction step described in Embodiment 3. However, in Embodiment 3, predicted duration of disease and/or disability is calculated, based on the predicted period of the person's healthy life expectancy estimated in the personal healthy life expectancy prediction step (step 75 in FIG. 10). In Embodiment 5, predicted duration of disease and/or disability is calculated, based on the predicted period of the person's healthy life expectancy expected, assuming that the person would practice life-style improvement advised in the health management plan.

FIG. 11 shows exemplary display content including predicted medical payment change calculated through the medical payment prediction step. This display example includes the duration of disease and/or disability and estimated medical expenses at the start of the practice according to the health management plan, at the present (during the practice), and at the achievement of the goal of the health management plan. The duration of disease and/or disability and estimated medical expenses at the start of the practice and at the present are calculated by the procedure illustrated in FIG. 10. The duration of disease and/or disability and estimated medical expenses at the achievement of the goal are calculated by the medical payment prediction step described in Embodiment 5. In the above display example, it is predicted that medical expenses of 12,000,000 yens are required at the initiation, whereas the predicted medical expenses are 10,000,000 yens at the present and 3,000,000 yens at the achievement of the goal: cut by 2,000,000 and cut by 9,000.000 respectively as compared with the amount at the initiation.

As described above, the health management support method of the present invention includes the medical payment prediction step in which the system calculates predicted medical payment change expected, assuming that the person would practice life-style improvement advised in the health management plan. A noticeable point of the benefit hereof is that the effect of the guidance for lifestyle-related diseases prevention such as advice about meals and advice about exercise can be represented by the index of medical payment that greatly influences the future life design of the person, thus making it possible to implement health management support that is quite effective for preventing diseases and doing self-healthcare.

While predicted duration of disease and/or disability is calculated by following the same procedure as described in Embodiment 3, it is also possible to use a procedure adapted for the healthy life expectancy prediction method applied in the health management effect prediction step. Although a period of healthy life expectancy at the assumed achievement of health screening results settled as the goal is predicted in the exemplary health management effect prediction procedure illustrated in FIG. 9, for example, duration of disease and/or disability at the achievement thereof may be predicted; in this case, the thus predicted duration is used in medical payment prediction.

Embodiment 6

Next, a preferred Embodiment 6 of the present invention will be described in detail, with reference to the appended drawings. Embodiment 6 concerns a medical insurer management support step 201 in which the system to carry out this invention supports the management of medical insurers, using the healthy life expectancy data. In Embodiment 6, illustrative embodiment of supporting the management of a predetermined medical insurer is explained.

Figure 22:
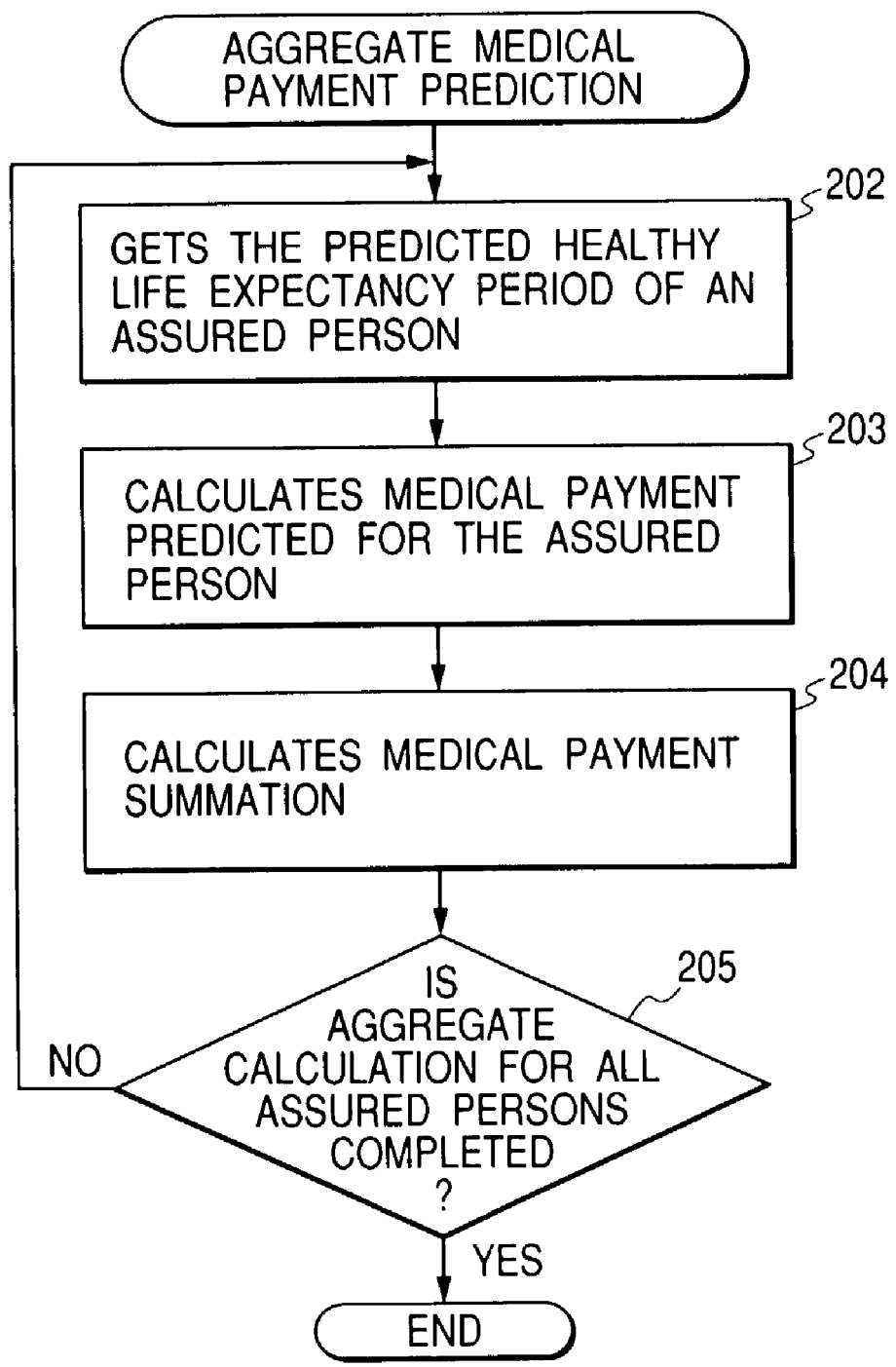
FIG. 22 illustrates an exemplary procedure of a medical insurer management support step included in the present invention.

The medical insurer management support step 201 is the step in which the system calculates the aggregate medical payment of the medical insurer for each person, based on the predicted healthy life expectancy periods of each assured person who is a policyholder insured by the medical insurer. FIG. 22 illustrates an exemplary procedure of predicting the aggregate medical payment in the medical insurer management support step. First, the system gets the predicted healthy life expectancy period of each assured person (step 202 in FIG. 22). This is implemented, for example, in such a way that the system determines whether to get the above period for each person, based on the content of the medical insurer information included in the health screening report data. Alternatively, this can be implemented in the following way. A list of the assured persons is prepared beforehand, each entry having personal identification information such as name, sex, and the date of birth of each assured person. The system checks matching of this information and the personal identification information in each individual health screening report data record.

Then, the system calculates medical payment predicted for each assured person from the healthy life expectancy data (step 203 in FIG. 22). This step is carried out by using the procedure described in Embodiment 3. Furthermore, the system calculates summation of the obtained medical payments predicted for each assured person (adding a newly calculated value to the previously calculated ones) (step 204 in FIG. 22). The above steps 202 to 204 are repeated for all those who are assured by the insurer (step 205 in FIG. 22).

Through the above procedure, the predicted amount of aggregate medical payment is obtained. FIG. 23 shows exemplary display contents including the predicted amount of aggregate medical payment thus obtained. The display content example 211 comprises the amount of aggregate medical payment (212) predicted, assuming that the assured persons would not practice life-style improvement advised in the health management plan and the corresponding amount (213) predicted, assuming the persons would do. This information is provided by the calculation according to the procedure illustrated in FIG. 22, wherein, for the predicted healthy life expectancy period used in medical payment calculation, that period predicted before the practice according to the health management plan and that period predicted as the result of the practice (as described in Embodiment 4) are assigned. The detail of the practice according to the health management plan and its expected effect vary for each assured person. Thus, the result of calculating the predicted amount of aggregate medical payment differs from the product of multiplying the predicted medical payment of each assured person by the number of the persons assured by the insurer.

As described above, the health management support method of the present invention includes the medical insurer management support step in which the system predicts the aggregate medical payment of an insurer as a whole, based on the predicted healthy life expectancy periods of each assured person who is a policyholder insured by the insurer. One noticeable point of the benefit hereof is enabling the medical insurer to reference the aggregate medical payment in future based on actual data and exactly budget for the payment, reflecting conditions varying for each assured person such as age, condition of health, and medical payment required in the budget. Another noticeable point of the benefit is enabling the medical insurer to grasp the effect of the practice according to the health management plan in terms of all the assured persons and evaluate the effect more exactly.

While summation of the medical payments predicted for all the assured persons is calculated and displayed in the above description of Embodiment 5, it is also possible to calculate and display average medical payments per year. Specifically, medical payments of all the assured persons are predicted per year, summed up, and displayed. As expressed by an equation 217 given in FIG. 23, where P(k) is the amount of medical payment of the assured person P predicted with regard to time k years later, summation of the amounts P(k) for all the assured persons equals to average medical payment a year. The amount P(k) is predicted by using the procedure described in Embodiment 3. Calculation of medical payment per year is executed with the equation 78 or 79 given in FIG. 21, wherein the payment is calculated year by year.

FIG. 23 includes another exemplary display content 214 of average medical payment per year, wherein payment is plotted along the ordinate over years to pass on the abscissa. Curve 215 represents payment predicted, assuming that the assured persons would not practice life-style improvement advised in the health management plan and line 216 represent payment predicted, assuming that the persons would do. A noticeable benefit hereof is that this graph wherein the transition of average medical payment per year is apparent helps the medical insurer exactly budget for the payment, develop management plans, and easily budget for the payment per year.

Embodiment 7

Next, a preferred Embodiment 7 of the present invention will be described in detail, with reference to the appended drawings. Embodiment 7 concerns a method for generating healthy life expectancy prediction data that is the basic data (healthy life expectancy prediction data) for predicting healthy life expectancy from healthy screening report data. This data is generated, using a diversity of healthy screening report data for a plurality of persons who underwent health screening and medical fee bill data records for past medical services rendered to the persons at medical institutions.

When a medical institution or the like renders medical services to a person, the medical institution bills the medical insurer for the person or some intermediary or audit corporation to charge the insurer some fees for the cost of rendering the service. The medical fee bill data comprises the information described on a bill of medical fees. This data comprises, for example, basic information, disease information, clinical process information, and charge information. The basic information is primary information about a fact that a medical institution rendered medical services to a person (patient). The basic information includes the person's (patient) name, sex, date of birth, medical insurer information (the name of the insurer, insurance card number, etc.), medical institution information (its address, name, telephone number, department name at which the person consulted a medical doctor, the name of the doctor, etc.), medical services type (out-patient, in-patient, etc.), exitus (transfer to another hospital, dead, etc, after the medical services), and so on. The disease information is primary information about what disease for which the patient consulted the doctor. The disease information includes, for example, the name of disease (name of injury/disease), medical services start date, the number of days the patient had medical services, cause of disease (injury) such as a traffic accident (job-related reason), and so on. The clinical process information is information about the clinical process or treatment taken for the patient, including, for example, type and number of times of process such as medical examination, medication, and an injection applied for the patient, and so on. The charge information is information about an amount of money the medical institution charges for the cost of the medical services, including, for example, unit cost per clinical process, medicine costs, total charge, and so on.

The medical fee bill data is data generated when a medical institution charges the medical insurer concerned some fees for the service rendered to the patient, whereas data on bills issued when a medical-care-related service provider (operator) bills the medical insurer concerned with service provision can be used. Specifically, nursing-care insurance bill data applied in the current nursing-care insurance system is used. Alternatively, accompanied by social security system reorganization, even if there would exist various insurance systems regarding medical care such as nursing-care insurance, medical insurers for the disability, medical insurers for the elderly (such as Medicare), regional medical insurers, and medical insurers for the business occupation, medical fee bill data generation is implemented by using data on bills issued when such service providers bill the medical insurers concerned.

Using the attached drawings, the method for generating healthy life expectancy prediction data, included in the present invention, will be detailed below.

Figure 13:
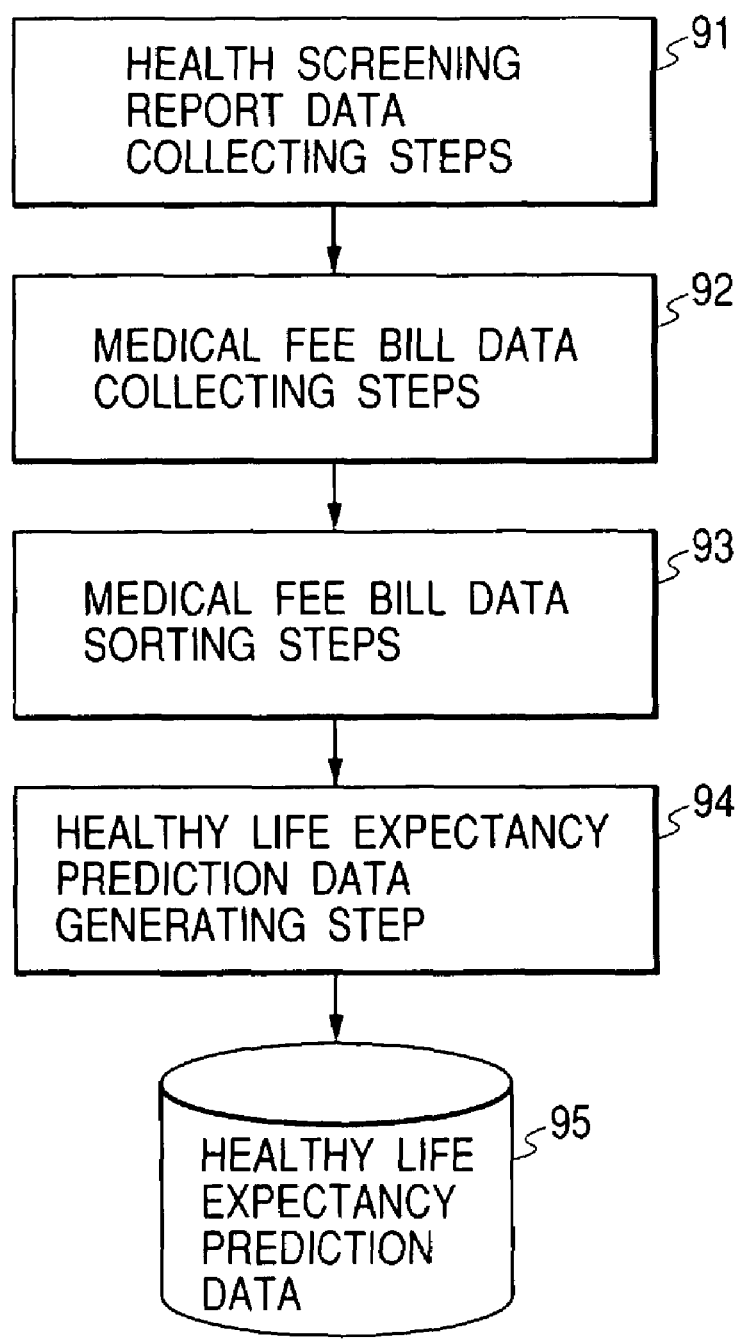
FIG. 13 is a process flowchart illustrating an example of the method for generating healthy life expectancy prediction data, included in the present invention.

FIG. 13 is a process flowchart illustrating an example of the method for generating healthy life expectancy prediction data, included in the present invention. In health screening report data collecting steps 91, the system to carry out this invention collects a diversity of health screening report data for a plurality of persons who underwent health screening. The thus collected health screening report data is stored in electronic form. Implementing these steps is basically the same as for the health screening report data entry step 11 included in FIG. 1; that is, data is collected by using networks, record media, image scanners, and the like. However, the health screening report data collecting steps include special steps for getting a diversity of health screening report data for a plurality of persons who underwent health screening; for example, a step of repeatedly collecting health screening report data until obtaining all prepared data.

In medical fee bill data collecting steps 92, the system collects medical fee bill data, each of which comprises medical services details and charges for the medical services rendered by a medical institution or the like to the person who underwent health screening. The thus collected medical fee bill data is stored in electronic form. Specifically, collecting such data is possible in ways that are exemplified below. The data is downloaded or distributed from health screening institutions, medical insurers, audit corporations, data maintenance service providers, etc. that maintain and manage obtained medical fee bill data in electronic form to the system via a network or record media. Alternatively, medical fee bills printed on paper are scanned by an image scanner, the characters and numeric values described thereon are recognized and transformed into electronic data, and the electronic data is transferred into the system. Alternatively, a keypuncher directly enters the information as described on medical fee bills in paper form and the system gets the keyed-in data.

In medical fee bill data sorting steps 93, the system sorts the collected medical fee bill data, according to the results specified in the health screening report data. That is, the system sorts the medical fee bill data by difference of health screening report data for each person who underwent health screening.

Figure 14:
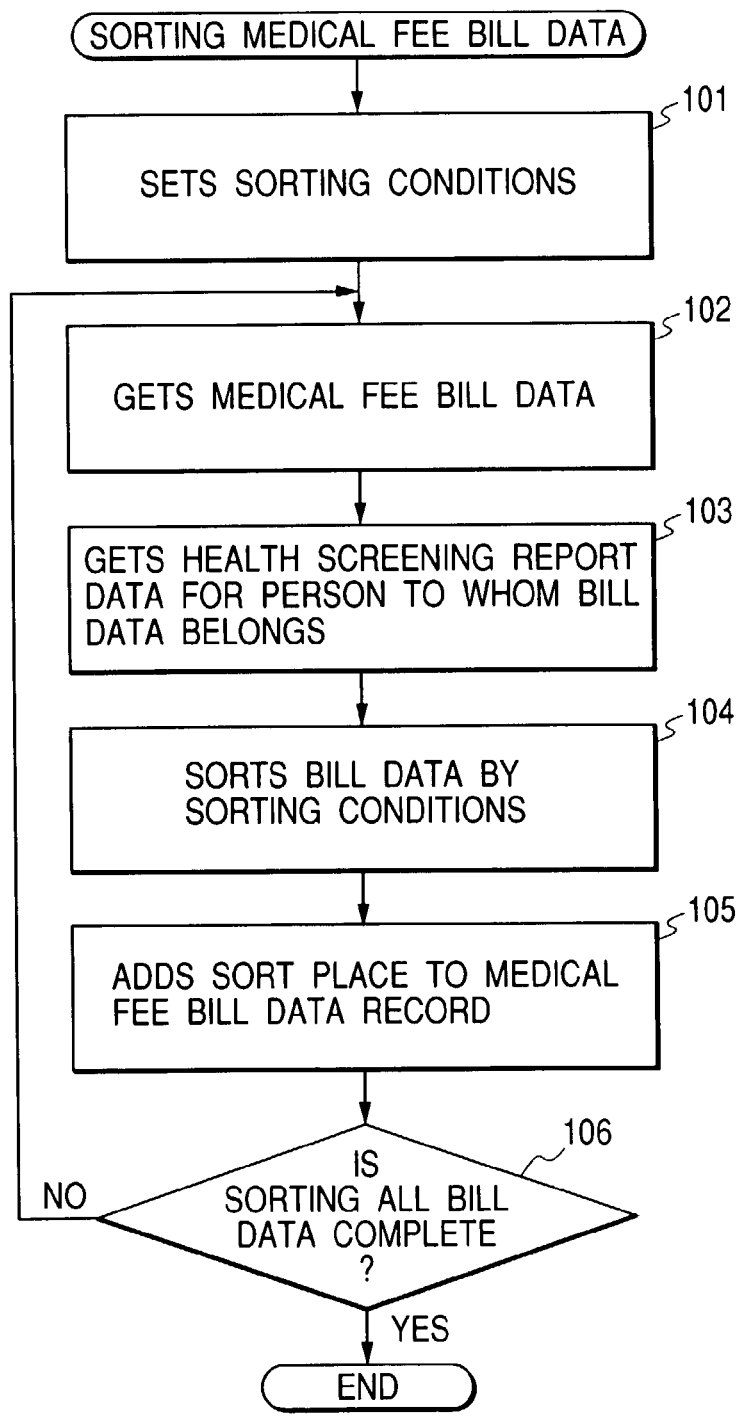
FIG. 14 illustrates an exemplary procedure of medical fee bill data sorting steps.

FIG. 14 illustrates an exemplary procedure of the medical fee bill data sorting steps. First, the system sets medical fee bill data sorting conditions (step 101 in FIG. 14). The sorting conditions are set by using the results specified in the health screening report data. For example, the conditions are set so that the data will be sorted, subject to the inquiry results (daily living habits about smoking, drinking, and exercise) and the decision results (obesity, hypertension, hyperlipemia, hyperglycemia, and hyperuricemia) in the health screening report data exemplified in FIG. 3. More specifically, the data will be sorted, depending on whether there are answers "Yes" to the above inquiry items (including any of three levels "No," "a little," and "much" for exercise) and according to the above abnormalities pointed out.

Then, the system gets one of the plurality of medical fee bill data records collected in the medical fee bill data collecting steps (step 102 in FIG. 14) and gets health screening report data for the person to whom the bill data obtained in the step 102 belongs from the plurality of health screening report data records collected in the health screening report data collecting steps. Then, the system determines a sort place by the contents of the health screening report data obtained in the step 103, according to the sorting conditions set in the step 101 (for example, the system determines what place of the health screening report data combinations shown in FIG. 3 to which the obtained report data is applicable). According to the report data, if, for example, the person has none of smoking, drinking and exercise habits and the examination results include a decision result of hyperuricemia, the system determines a sort place corresponding to the position of a graph 27 given in FIG. 3.

Finally, the system sorts the medical fee bill data obtained in the step 102 by the sort place determined in the step 104 (step 105 in FIG. 14). In this example, to the sorted medical fee bill data record, a storage field to contain its sort place is added so that the sort place is stored. The system ascertains whether sorting all medical fee bill data is complete (step 106 in FIG. 14); if not complete, the system gets new medical fee bill data in the step 102 and automatically repeats the following steps up to the step 105.

Leaving the procedure of the medical fee bill data sorting steps, return to FIG. 13.

In a healthy life expectancy prediction data generating step 94, the system generates healthy life expectancy prediction data, the basic data for predicting healthy life expectancy from healthy screening report data. Using the medical fee bill data sorted by difference of health screening report data in the medical fee bill data sorting steps, the system calculates the percent of the dead and the percent of people being sick or disabled for every age. Based on the result of this calculation, the system generates healthy life expectancy prediction data 95.

Figure 15:
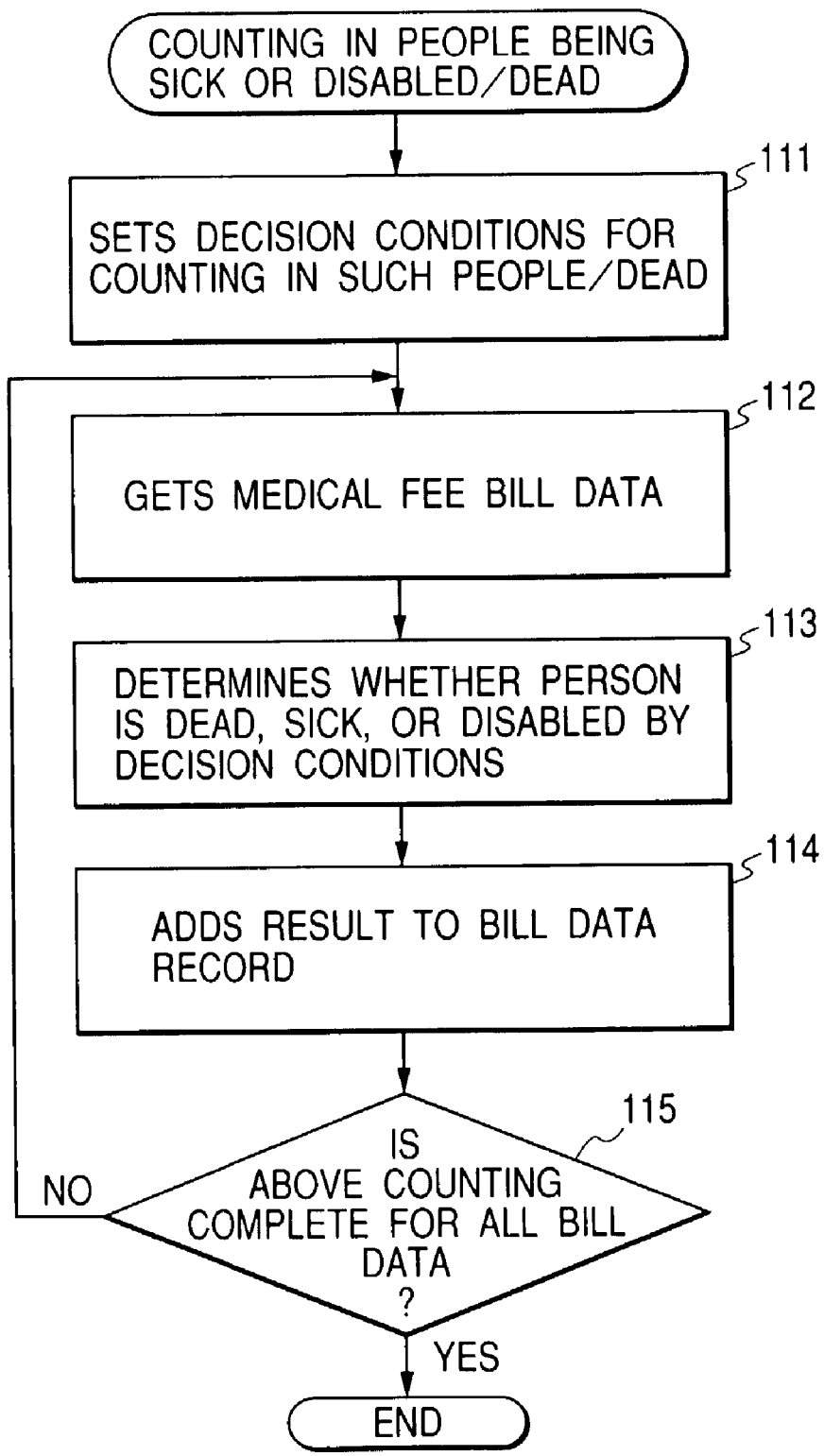
FIG. 15 illustrates an exemplary procedure of a healthy life expectancy prediction data generating step.

FIG. 15 illustrates an exemplary procedure of the healthy life expectancy prediction data generating step. First, the system sets decision conditions for counting the dead and the people who need help of someone else, being sick or disabled (step 111 in FIG. 15). The condition for counting the dead is set as follows: if, for example, "dead" is specified as exitus included in the basic information of medical fee bill data, the system counts it. As for the people being sick or disabled, the conditions for counting them is set, based on a diversity of information such as basic, disease, clinical process, and charge information.

Figure 16:
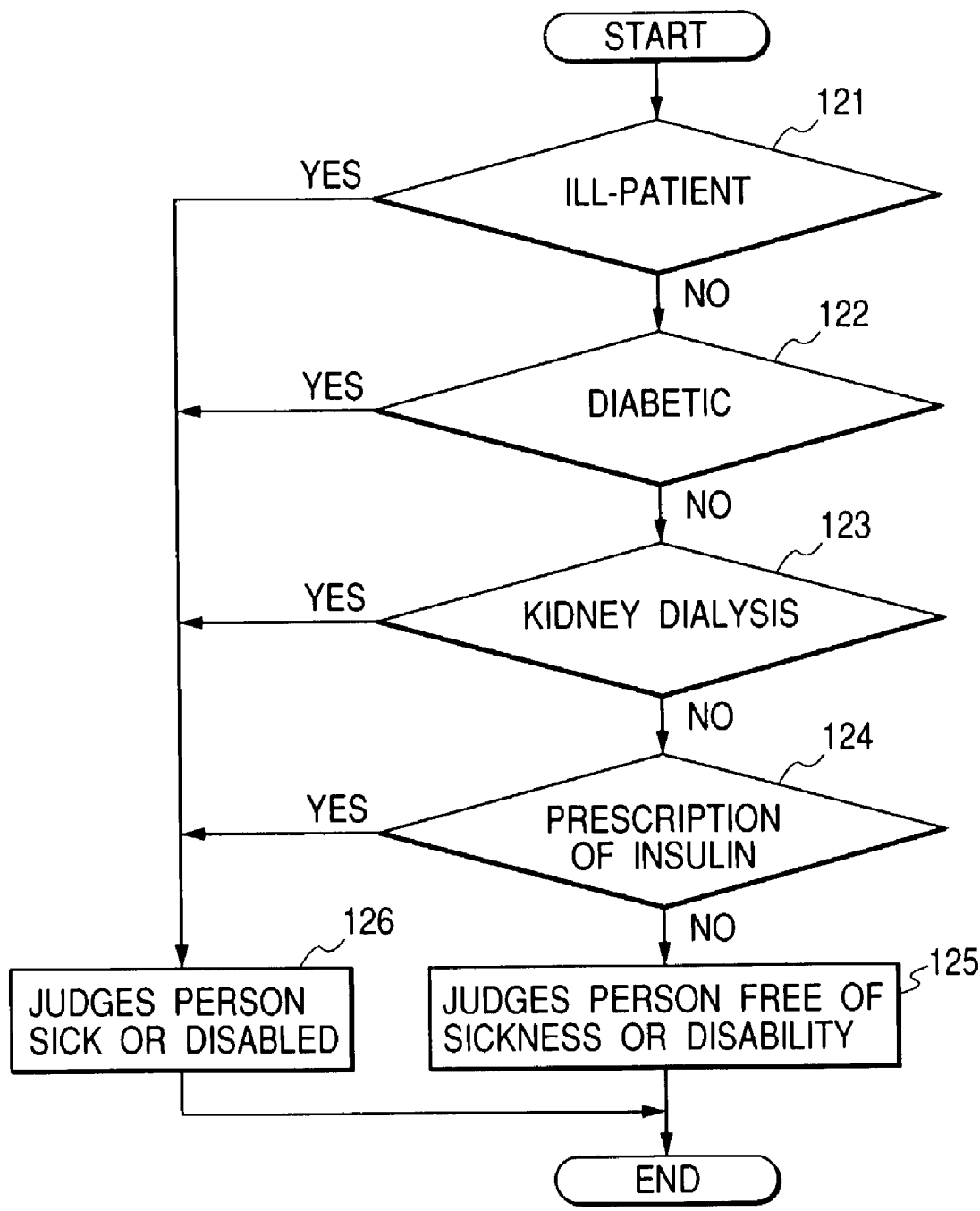
FIG. 16 illustrates exemplary conditions by which to determine that a person is sick or disabled.

FIG. 16 illustrates exemplary conditions by which the system determines that a person is sick or disabled. The system judges whether the person is an in-patient by the medical services type within the basic information (step 121 in FIG. 16). The system judges whether the person is a diabetic by the name of injury/disease within the disease information (step 122 in FIG. 16). The system judges whether the person is treated with kidney dialysis by the treatment specified within the clinical process information (step 123 in FIG. 16) . The system judges whether the prescription of insulin is applied for the person by the medication specified within the clinical process information (step 124 in FIG. 16) . If at least one of the above specifics is true during the steps 121 to 124, the system judges the person sick or disabled and counts the person as one of the people being sick or disabled (step 126 in FIG. 16). If none of the above particulars is true, the system judges the person free of the sickness or disability and does not count the person (step 125 in FIG. 16).

Return to FIG. 15. Then, the system gets one of the medical fee bill data records on a personal basis placed under the same sort of health screening report data (step 112 in FIG. 15) . By referring to the medical fee bill data obtained in the step 112, the system determines whether the person in question (the customer of the medical institution) is applicable to (1) the dead or (2) the people who need help of someone else, being sick or disabled, by the count-in conditions set in the step 111 (step 113 in FIG. 15). Finally, the system adds the result of determination made in the step 113 to the record of the bill data (step 114 in FIG. 15). In this example, to the medical fee bill data record, a storage field to contain the result of determination is added so that this result is stored. The system ascertains whether the above determination and count are complete for all medical fee bill data records (step 115 in FIG. 15); if not complete, the system gets new medical fee bill data record in the step 112 and automatically repeats the following steps up to the step 114. The system automatically repeats the above steps in the same procedure for medical fee bill data records placed under other sorts of health screening report data.

By the above-described procedure, the number of the dead and the number of people being sick or disabled are obtained from all the medical fee bill data records sorted by difference of health screening report data. Age information also is obtained from the medical fee bill data records by referring to the date of birth within the basic information. From the statistics of the dead and the people being sick or disabled and their age, thus, the percent of the dead and the percent of the people being sick or disabled for every age are derived.

Finally, from the thus obtained statistics of the percentages of the dead and people being sick or disabled on a per-age basis, the system generates data corresponding to the curve 23 in the graph shown in FIG. 2, that is, healthy life expectancy prediction data. Specifically, this data can be generated in the following way. For all sorts by difference of the results specified in the health screening report data (that is, sorts set in the step 101 in FIG. 14), the proportion of normal people to the total number of the persons who underwent health screening is calculated on a per-age basis. Hereon, the number of normal people is obtained by subtracting the number of the dead and the number of the people being sick or disabled from the total number of the persons who underwent health screening.

Leaving off the explanation of the procedure of the healthy life expectancy prediction data generating step, now, Embodiment 7 will be fully explained.

As a first feature of Embodiment 7, the method for generating healthy life expectancy prediction data, included in the present invention, as described above, enables the system to generate the basic data (healthy life expectancy prediction data) for predicting healthy life expectancy from healthy screening report data, using a diversity of healthy screening report data for a plurality of persons who underwent health screening and medical fee bill data records for past medical services rendered to the persons at medical institutions. A noticeable point of the benefit hereof is making it possible to generate healthy life expectancy prediction data differentiated by health screening report data, using only the information obtained when each person underwent health screening and when each person had medical services at any medical institution. Otherwise, such data generation would require a lot of labor and time for a special survey and related work.

As a second feature of Embodiment 7, the method for generating healthy life expectancy prediction data, included in the present invention, generates the system to automatically sort the medical fee bill data records on a personal basis by sorting conditions that has been set beforehand through the use of the results specified in the health screening report data. As a third feature of Embodiment 7, the method for generating healthy life expectancy prediction data, included in the present invention, enables the system to automatically determine whether the person in question is sick or disabled, according to predetermined conditions for this determination, referring to the medical fee bill data records on a personal basis and count the number of people being sick or disabled. One noticeable point of the benefit hereof is making it possible to do high-speed processing of a great quantity of medical fee bill data without employing manual labor. Another noticeable point of the benefit is making it possible to always apply the same sorting conditions and decision conditions even for distributed processing across a plurality of devices and during long-period processing, thus eliminating difference across devices and variation over time and calculating the percent of people being sick or disabled with accuracy.

While, in the above description of Embodiment 7, determination as to whether the person is sick or disabled is made by using the medical fee bill data records, it is also possible to use another information or combination of a plurality of information to make such determination. For example, the following information is used. If the questionnaire for health screening includes an item, degree of living on your own, the answer to this question is used. Information about nursing care rendering such as a nursing-care insurance system is used. Survey reports of this subject made by public health nurses are used. Alternatively, a plurality of medical fee bill data records is used to make the above determination. Specifically, for example, the system gets a plurality of medical fee bill data records for different periods of medical services for a person. Referring to the disease information within the above records, the system determines that the person is sick or disabled if long-period medical services were rendered to the person for a specific disease. This enables the system to determine whether the person is sick or disabled with increased accuracy and generate accurate healthy life expectancy prediction data.

While, in the above description of Embodiment 7, the system generates healthy life expectancy prediction data from the per-age basis statistics of the number of the dead and the number of people being sick or disabled, it is also possible to generate other data at the same time. For example, data corresponding to the curve 22 in the graph shown in FIG. 2 (transition of the percent of live people over ages) is generated. Specifically, this data can be generated by calculating the proportion of live people to the total number of the persons who underwent health screening on a per-age basis for each of the sorts by difference of the results specified in the health screening report data. Hereon, the number of live people is obtained by subtracting the number of the dead from the total number of the persons who underwent health screening. In addition to healthy life expectancy, it is also possible to calculate average life expectancy and duration of disease and/or disability (the period of the life state being sick or disabled).

While, in the above description of Embodiment 7, the system generates healthy life expectancy prediction data from the per-age-basis statistics of the number of the dead and the number of people being sick or disabled, its is also possible to generate data using another method. For example, by following up the records of medical fee bill data, statistics are obtained about the following during a transitional period: those who became sick or disabled, those who died, those who remain normal among normal people; and those who died, those who became normal, and those who remain sick or disabled among sick or disabled people. From the number of the persons who remain normal and the number of the persons who became normal among sick or disabled people during the transitional period, the number of normal people is calculated. In this way, healthy life expectancy prediction data can be generated. Based on the change in the number of normal people, the number of sick or disabled people, and the number of the dead, the above calculation can be executed. Thus, even if the percentage of sick or disabled people and the percentage of the dead greatly change, prediction data can be generated with accuracy.

In the above description of Embodiment 7, the system generates healthy life expectancy prediction data, based on the per-age-percentages of normal people at the time of this data generation, on the assumption that these percentages will remain invariable in future. It is also possible to generate such data by following up the percentages over the ages from the birth to the occurrence of a disease or disability or combining both methods. Continuos survey data rather than fragmentary statistical data can be used and prediction data can be generated with increased accuracy.

Embodiment 8

Next, a preferred Embodiment 8 of the present invention will be described in detail, with reference to the appended drawings. In the foregoing Embodiment 7, the process was illustrated that generates healthy life expectancy predication data, using a diversity of healthy screening report data for a plurality of persons who underwent health screening and medical fee bill data records for past medical services rendered to the persons at medical institutions. To carry out this process, it is necessary to interlink health screening report data and medical fee bill data for each person who underwent health screen and had medical services. Embodiment 8 is an exemplary step for carrying out this interlinking (data integration step).

In embodiment 8 of the invention, data interlinking is performed by primarily using the information included in a health screening report data record and the information included in a medical fee bill data record. There is no problem when both records include common information by which the person to whom each record belongs can be identified. In actual circumstances, however, health screening report data and medical fee bill data are generated by different institutions or corporations and maintained in different methods. Moreover, the health screening institutions apply their specific data management methods suitable for their duties. For these reasons, it is possible that the above common information does not exist. Embodiment 8 enables data interlinking even if common person-identifiable information does not exist (or this information exists, but is not sufficient).

Figure 17:
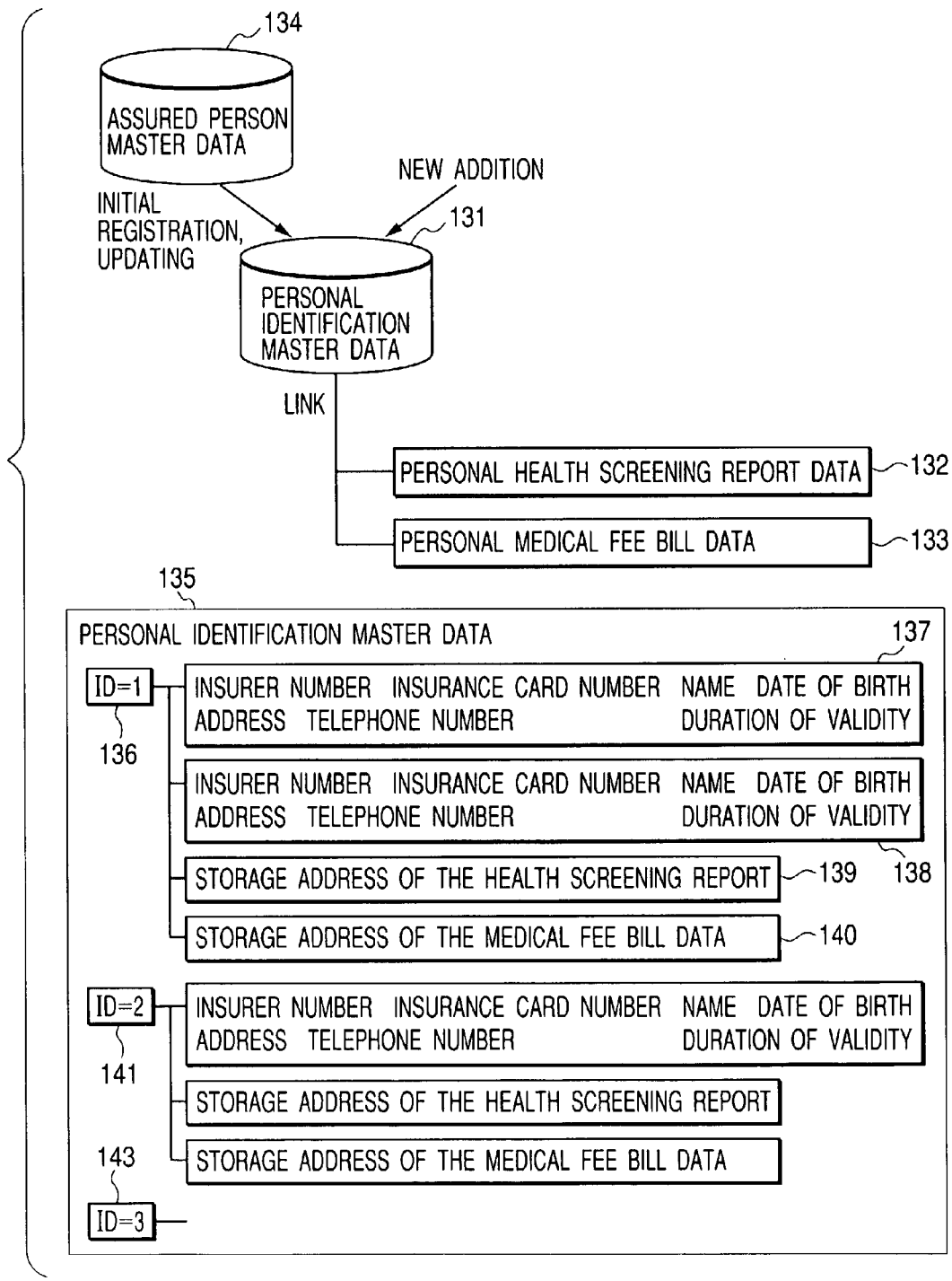
FIG. 17 is a schematic drawing illustrating an example of a data integration step included in the present invention.

FIG. 17 is a schematic drawing illustrating an example of the data integration step included in the present invention. In this step, the system interlinks health screening report data and medical fee bill data for each person who underwent health screening, using personal identification master data 131. The personal identification master data 131 comprises personal identifiers (IDs) (136, 141, and 143), each identifying a person registered with the personal identification mater database, personal identification information (137, 138) that is basic information about the person, the storage address of health screening report data (139) that points at the address where the personal health screening report data is stored, the storage address of medical fee bill data (140) that points at the address where the personal medical fee bill data record is stored. The storage address of health screening report data and the storage address of medical fee bill data are stored, functioning as the link-to-address pointers to point at the actual address where the personal health screening report data 132 is stored and the actual address where the personal medical fee bill data 133 is stored.

The personal identification information is to identify the person to which a health screening report data record and a medical fee bill data record belong. As this information, a diversity of the person-identifiable information is stored (such as the person's name, date of birth, address, telephone number, and information about the medical insurer of the medical insurance that the person joined, etc.) A plurality of personal identification information sets can be assigned to one personal ID to be adaptable to change in the information content, such as address change and medical insurer change; moreover, each information set includes duration of validity.

Registering data with and updating the personal identification master database are performed at a proper time and in an appropriate manner, for example, using assured person master data 134 (a database for storing basic information about the assured persons who joined any insurance provided by any medical insurer). Alternatively, new data is added to the personal identification master database in the data integration step included in the present invention. The assured person master database stores the medical insurer identifier number, insurance card number, name, the person's date of birth, address, telephone number, date of insurance acquisition, date of insurance term expiry, etc for each assured person.

Figure 18:
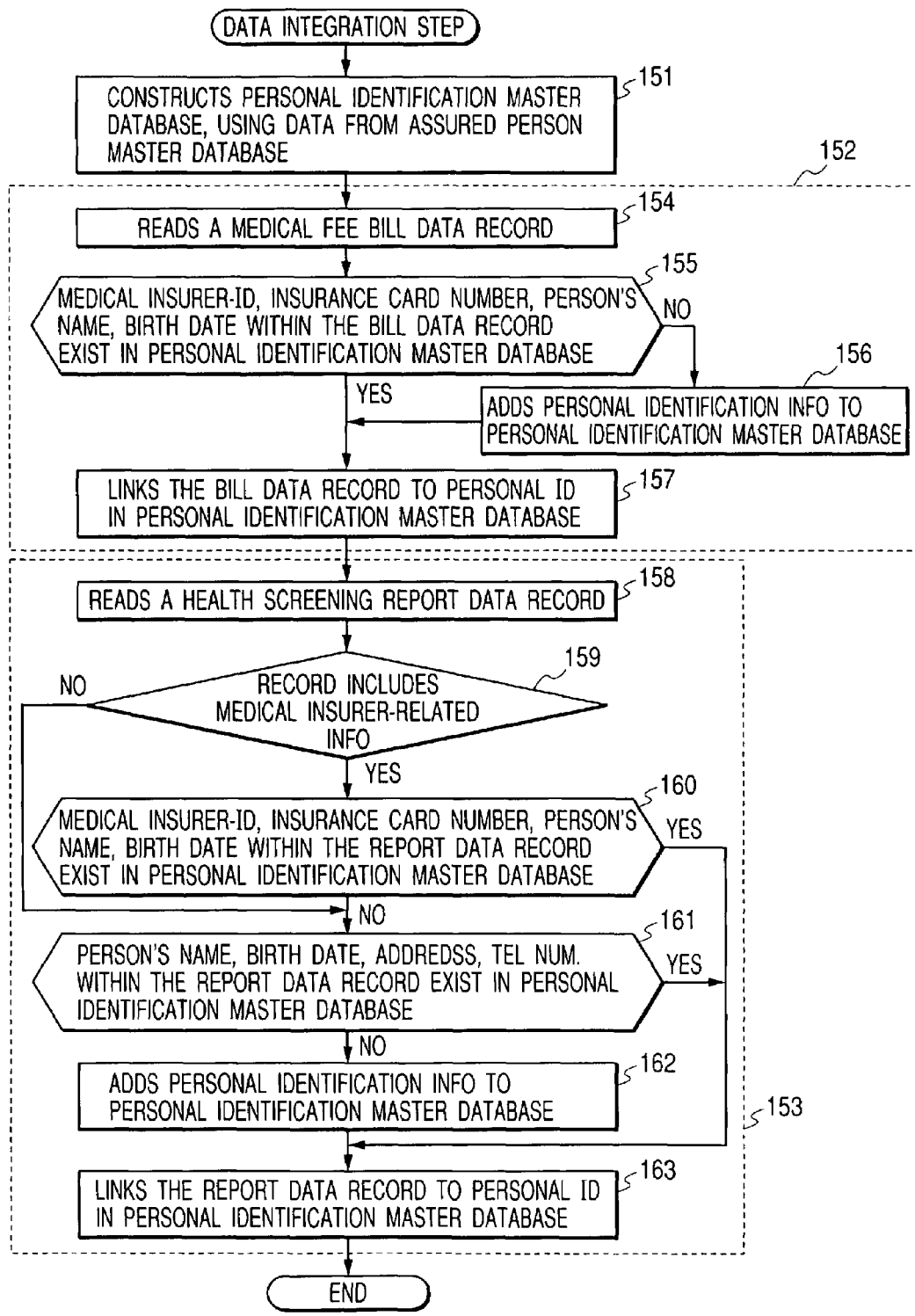
FIG. 18 illustrates an exemplary procedure of the data integration step included in the present invention.

FIG. 18 illustrates an exemplary procedure of the data integration step included in the present invention. In the data integration step, using personal IDs, the system to carry out this invention manages health screening report data and medical fee bill data for a person who is identified by personal identification information. First, as pre-processing, the system constructs the personal identification master database, using data from the assured person master database (151). Specifically, the system registers the assured persons and their information stored in the assured person master database into the personal identification master database. The system registers duration of validity, using the date of insurance acquisition and the data of insurance term expiry. After the pre-processing, the system executes a step 152 for linking medical fee bill data to the personal ID of the person to whom the bill data belongs and a step 153 for linking health screening report data to the personal ID of the person to whom the report data belongs.

The step 152 regarding medical fee bill data is carried out as follows. First, the system reads a record of medical fee bill data (154). The system searches the personal identification master database for personal identification information matching with the person-identifying information (medical insurer identifier number, insurance card number, and the person's name and date of birth) within the bill data record (155). If matched information exists, the system links the medical fee bill data record to the personal ID (157). In fact, the system assigns the link-to-address of the medical fee bill data record to the storage address of medical fee bill data within the personal identification information with that personal ID. Unless matched information exists, the system registers the person to whom the bill data belongs with the personal identification master database as new entry. In fact, the system generates a new personal ID and personal identification information for the person and stores them into the personal identification master database (156). Then, the system links the medical fee bill data record to the new personal ID (157).

In the above step 155, if a plurality of personal identification information sets with different duration of validity exists under the same personal ID, the system selects the appropriate one by referring to the time-related information within the medical fee bill data record, for example, medical services start date included in the disease information thereof.

The step 153 regarding health screening report data is carried out in such a way that will be described below, wherein, by way of example, the system is handling two health screening reports created at different screening institutions (health screening report data A and health screening report data B). The health screening report data A includes medical insurer information as basic information and the health screening report data B does not include this information.

First, the system reads a record of health screening report data (158) and checks to see whether medical insurer information is included therein as basic information (159). If this information is included (health screening report data A), the system searches the personal identification master database for personal identification information matching with the person-identifying information (medical insurer identifier number, insurance card number, and the person's name and date of birth) within the report data record (160). If matched information exists, the system links the health screening report data record to the personal ID (163) as does in the step 157 for medical fee bill data.

If medical insurer information is not included as basic information (health screening report data B), as the result of the check in the step 159, or if matched personal identification information does not exist, as the result of the search in the step 160, the system again searches the personal identification master database for personal identification information, without using medical insurer information (medical insurer identifier number and insurance card number). In fact, the system searches the personal identification master database for personal identification information matching with the person-identifying information (the person's name, date of birth, address, telephone number, etc.) within the report data record, as does in the step 160.

Hereon, the person's address and telephone number are not included in the basic information of medical fee bill data and cannot be used as the person-identifying information common for report data and bill data. However, the method according to the present invention enables the system to register the person's address and telephone number stored in the assured person master database into the personal identification master database to make them join the set of medical insurer identifier number, insurance card number, and the person's name and date of birth (151), and therefore the person is identifiable for both data.

As the result of the step 160, if matched information exists, the system links the health screening report data record to the personal ID (163). Unless matched information exists, the system registers the person to whom the report data belongs with the personal identification master database as new entry. In fact, the system generates a new personal ID and personal identification information for the person and stores them into the personal identification master database (162). Then, the system links the health screening report data record to the new personal ID (163).

In the above steps 160 and 161, if a plurality of personal identification information sets with different duration of validity exist under the same personal ID, the system selects the appropriate one by referring to the time-related information within the health screening report data record, for example, the date of execution of screening included in the basic information thereof.

According to the above-described procedure of the step 152 regarding medical fee bill data and the step 153 regarding health screening report data, the system handles all health screening report data records collected in the health screening report data collecting steps 91 and all medical fee bill data records collected in the medical fee bill data collecting steps 92. Thereby, the health screening report data records and medical fee bill data records can be interlinked on a person-by-person basis.

In the present invention, the method for generating healthy life expectancy prediction data includes the data integration step wherein, as described above, the system interlinks health screening report data and medical fee bill data on a person-by-person basis, using person-identifiable information included in health screening report data records and person-identifiable information included in medical fee bill data records. A noticeable merit hereof is making it possible to generate healthy life expectancy prediction data.

More specifically, in the above integration step, a personal identification information database storing a diversity of person-identifiable information is prepared so that the system will identify a person to whom a health screening report data record and a medical fee bill data record belong, referring to personal identification information from the database, wherein management is made with personal IDs assigned to the entries per person. If personal identification information within a record of the above data does not exist in the database, it is registered as a new entry with a new personal ID. Thus, even if person-identifiable information common for both records does not exist (exits, but is not sufficient), the system can interlink health screening report data and medical fee bill data record for a person. A noticeable merit hereof is making it possible to generate healthy life expectancy prediction data, using more health screening report data and medical fee bill data and increase the accuracy of healthy life expectancy prediction data.

In the present invention, the personal identification master database stores a diversity of personal identification information and the system identifies a person to whom a health screening report data record and a medical fee bill data record belong by checking a match between the information for the person stored in the database and the corresponding information included in both records. It is also possible to incorporate a step for determining whether matching occurs, not only simply checking name and address matching included in the above information. For example, a step can be incorporated to allow for the following. If a person continues to have medical services even after his or her insurance term expires, which is allowed as an exceptional case provided in a insurance system, the system determines whether the duration of validity is consistent with the medical services start date derived from his or her medical fee bill data, according to the provisions of the insurance system. Alternatively, for a health screening report data record and a medical fee bill data record that do not match completely, but partially match with the relevant personal identification information, a flag which is prepared beforehand within them is set, so that, later, an operator will be able to interactively determine whether matching occurs. Interlinking health screening report data and medical fee bill data can be performed more exactly and the accuracy of healthy life expectancy prediction data can be further increased.

Embodiment 9

Next, a preferred Embodiment 9 of the present invention will be described in detail, with reference to the appended drawings.

Figure 12:
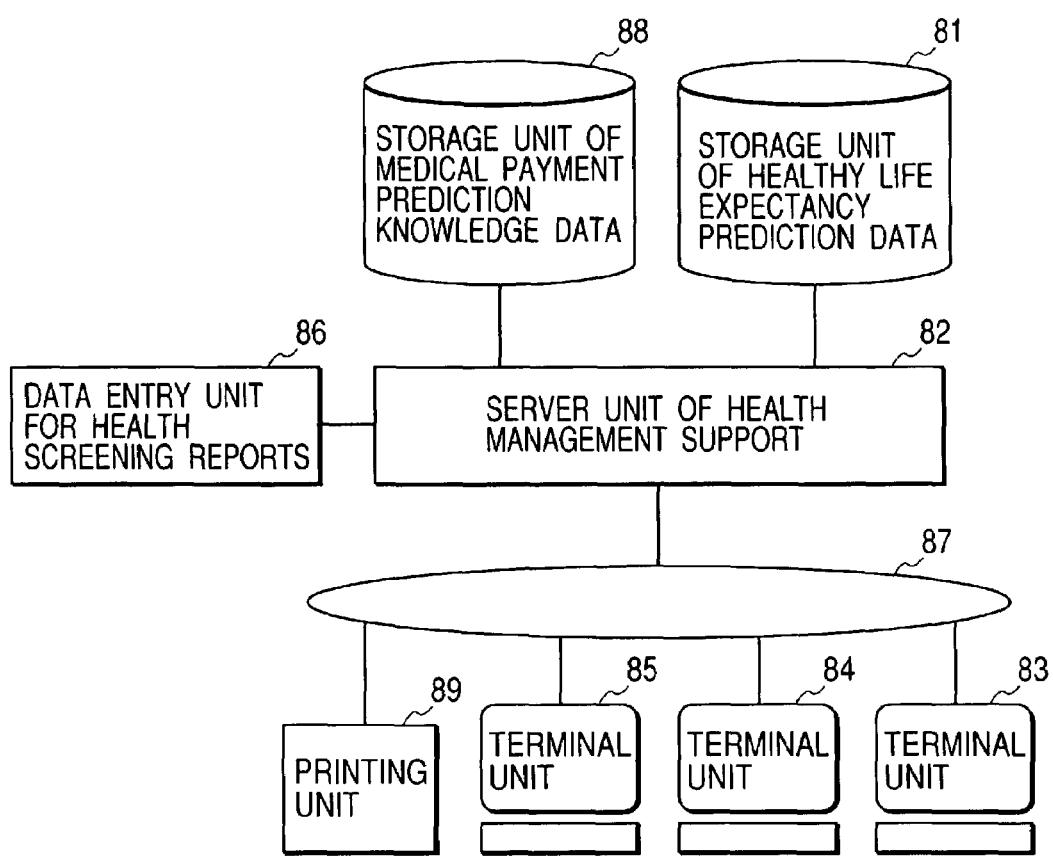
FIG. 12 is a structural diagram for explaining an exemplary health management support system of the present invention.

FIG. 12 is a structural diagram for explaining an exemplary health management support system of the present invention. Reference numeral 81 denotes a storage unit of healthy life expectancy prediction data in which healthy life expectancy prediction data is stored as the basic data for predicting healthy life expectancy from health screening report data. Specifically, this storage unit is a database embodied in magnetic disks or other storage media, semiconductor memories, etc.

Reference numeral 82 denotes a server unit of health management support that estimates a predicted period of personal healthy life expectancy and generates information about health management, based on the predicted period estimated. Specifically, the server is embodied in a general-purpose computer or the like. Reference numerals 83, 84, and 85 denote terminal units on which information about health management generated by the server unit of health management support is displayed. Specifically, each terminal is embodied in a computer with a display device such as a CRT display or a liquid crystal display.

Reference numeral 86 denotes a data entry unit for health screening reports that is used to input health screening report data in electronic form for persons who underwent health screening to the system. Specifically, the data entry unit is embodied in a computer connectable to a network to which health screening institutions, medical insurers, business establishments, data maintenance service providers, etc. may connect, an OCR device for scanning such reports printed on paper and generating electronic data thereof, or a computer or the like with a keyboard input device by which the written data of such reports is keyed in.

Reference numeral 88 denotes a storage unit of medial payment prediction knowledge data in which medical payment prediction knowledge data is stored as the basic data for predicting medical payment by considering estimated healthy life expectancy. This storage unit can be embodied in the same way as for the storage unit of healthy life expectancy prediction data. Reference numeral 89 denotes a printing unit that prints out information about health management generated by the server unit of health management support. Reference numeral 89 denotes a network for information transmission, by which the server unit of health management support 82, terminal units 83 to 85, and printing unit 89 are connected. Specifically, the network is embodied by using leased lines, the Internet, or any other type of network.

The terminal units 83 to 85 are located at homes or the like where the participants joined a heath screening support program can use at any time. These units can be located in places where doctors, public health nurses, or business establishment's personnel in charge of employee health management can use, who work at any of the following organizations that provide health management support: health screening institutions, public health centers, administrative organs, medical insurers, business establishments, etc.

The present system is able to implement the processing steps of the health management support method of the present invention. Specifically, the processing steps (10 to 18) mentioned in FIG. 1 are primarily carried out by the server unit of health management support 82. However, the health screening report data entry step 11 is carried out by the data entry unit for health screening reports 86, the display step 15 is carried out by the terminal units 83 to 85, and the printing step 16 is carried out by the printing unit 89. Healthy life expectancy prediction data 19 is stored in the storage unit of healthy life expectancy prediction data 81 and medical payment prediction knowledge data 20 is stored in the storage unit of medial payment prediction knowledge data 88.

In the following, an example of how the health management support method is put into effect by the components of the health management support system of the present invention will be explained. In this example, the following explanation focuses on an example of implementing the steps for displaying or printing predicted personal healthy life expectancy periods and related information described in Embodiment 1.

Using the data entry unit for health screening reports 86, the input of health screening report data for each person who underwent health screening to the system is first performed as per the health screening report data entry step 11. The thus input health screening report data is transferred to the server unit of health management support 82.

Then, the server unit of health management support 82 estimates personal healthy life expectancy, based on the health screening report data. This estimation is carried out as per the personal healthy life expectancy prediction data generating step 12 and the personal healthy life expectancy prediction step 13. The healthy life expectancy prediction data necessary for carrying out the personal healthy life expectancy prediction data generating step 12 is retrieved from the storage unit of healthy life expectancy prediction data 81.

Finally, the predicted healthy life expectancy periods and related information estimated by the server unit of health management support 82 are transmitted to the terminal units 83 to 85 over the network and displayed. Displaying is performed as per the display step 15. The above periods and related information are also transmitted to the printing unit 89 over the network 87 and printed out.

Further processing steps of health management support using the predicted healthy life expectancy periods described in Embodiments 2 to 6 are implemented by the server unit of health management support 82. Specifically, these steps are the health management plan generation step 17 (health screening plan generation steps (FIG. 6) and healthy life-style plan generation steps (FIG. 7)), medical payment prediction step 18, health management effect prediction step 14, and medical payment prediction step 10. The medical payment prediction knowledge data necessary for carrying out the medical payment prediction step 18, health management effect prediction step 14, and medical payment prediction step 10 is retrieved from the storage unit of medial payment prediction knowledge data 88. The exemplary display contents and printouts illustrated in FIGS. 4, 5, 8, and 11 are displayed and printed by the terminal units and the printing unit.

As described above, the health management support system of the present invention includes the server unit of health management support that estimates a predicted period of healthy life expectancy on a person-by-person basis, using the health screening data for each person who underwent health screening, input through the data entry unit for health screening reports, and the healthy life expectancy prediction data stored in the storage unit of healthy life expectancy prediction data, and generates information about health management, based on the predicted periods thus estimated. A noticeable point of the benefit hereof is enabling each person who underwent health screening to grasp his or her health condition quantitatively, based on the index of healthy life expectancy, and making it possible to develop health management plans based on healthy life expectancy and predict health management effects, which could boost the person's will to prevent diseases and do self-healthcare.

Embodiment 10

Next, a preferred Embodiment 10 of the present invention will be described in detail, with reference to the appended drawings.

Figure 19:
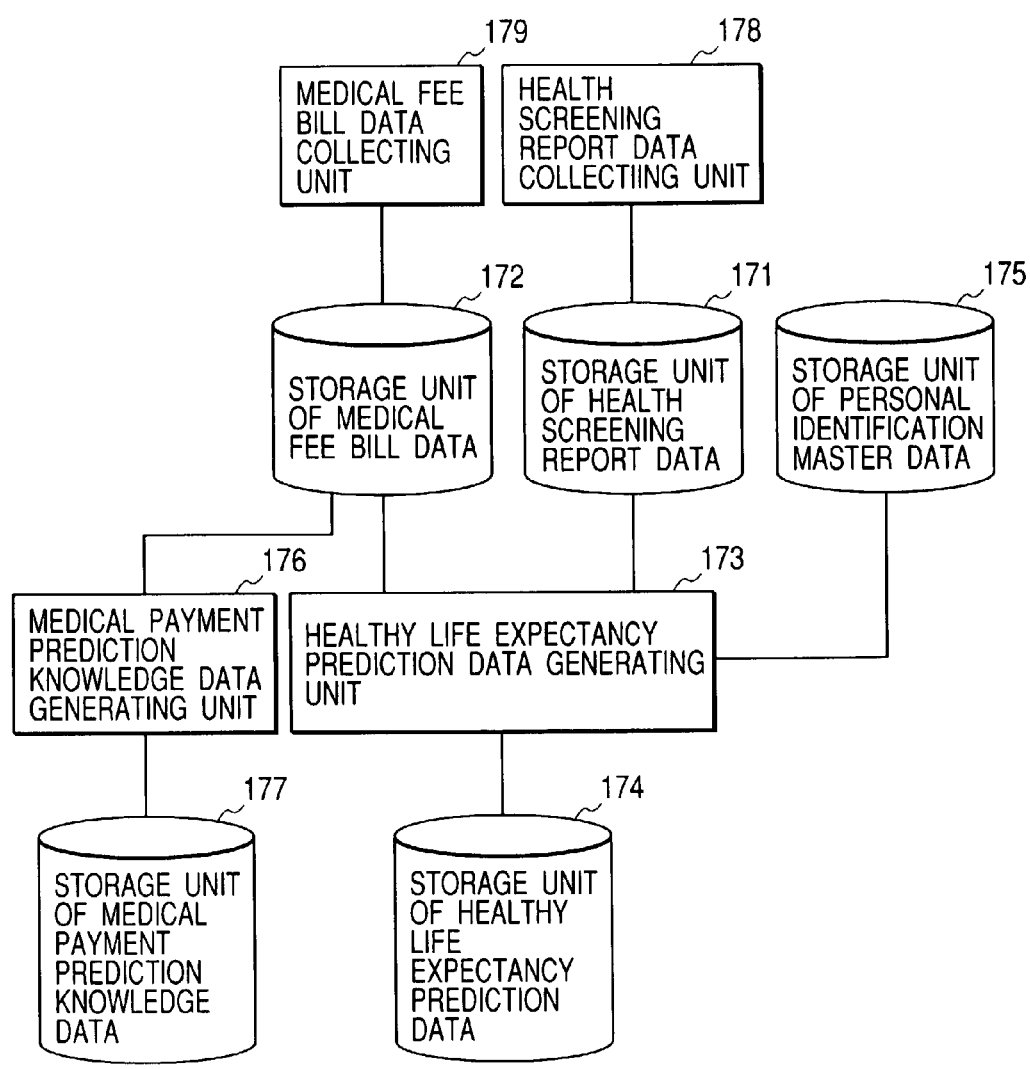
FIG. 19 is a structural diagram for explaining an exemplary system for generating healthy life expectancy prediction data, included in the present invention.

FIG. 19 is a structural diagram for explaining an exemplary system for generating healthy life expectancy prediction data, included in the present invention. Reference numeral 171 denotes a storage unit of health screening report data in which a diversity of health screening report data for a plurality of persons who underwent health screening is stored. Reference numeral 172 denotes a storage unit of medical fee bill data in which medical fee bill data is stored, comprising a diversity of medical services details and charges for a plurality of consumers of medical institutions.

Reference numeral 173 denotes a healthy life expectancy prediction data generating unit that generates healthy life expectancy prediction data as the basic data for predicting healthy life expectancy from the health screening report data. Reference numeral 174 denotes a storage unit of healthy life expectancy prediction data in which healthy life expectancy prediction data generated by the healthy life expectancy prediction data generating unit is stored.

Reference numeral 175 denotes a storage unit of personal identification master data in which information required for interlinking health screening report data and medical fee bill data for each person who underwent health screening is stored.

Reference numeral 178 denotes a health screening report data collecting unit that collects health screening report data from health screening institutions, medical insurers, and business establishments, etc. that maintain and manage obtained health screening report data and data maintenance service providers or the like. Reference numeral 179 denotes a medical fee bill data collecting unit that collects medical fee bill data from medical institutions, medical insurers, etc. that maintain and manage obtained medical fee bill data and data maintenance service providers or the like.

The storage units 171, 172, 174, and 175 are specifically databases embodied in magnetic disks or other storage media, semiconductor memories, etc. The unit 173 is specifically embodied in a general-purpose computer or the like. The units 178 and 179 are embodied in computers connectable to a computer network formed by leased lines or using the Internet or any other type of network.

The system for generating healthy life expectancy prediction data is able to implement the processing steps of the method for generating healthy life expectancy prediction data included in the present invention. Specifically, the processing steps (91 to 94) mentioned in FIG. 13 are carried out by the healthy life expectancy prediction data generating unit 173. Generated healthy life expectancy prediction data 95 is stored into the storage unit of healthy life expectancy prediction data 174.

In the following, an example of bringing the method for generating healthy life expectancy prediction data into effect by the system for generating healthy life expectancy prediction data included in the present invention will be explained. In this example, the following explanation focuses on an example of implementing the steps for generating healthy life expectancy prediction data described in Embodiment 7.

First, the health screening report data collecting unit 178 collects a diversity of health screening report data as per the health screening report data collecting steps 91. The collected health screening report data is stored into the storage unit of health screening report data 171. Moreover, the medical fee bill data collecting unit 179 collects a diversity of medical fee bill data as per the medical fee bill data collecting steps. The collected medical fee bill data is stored into the storage unit of medical fee bill data 172.

Then, the healthy life expectancy prediction data generating unit 173 generates healthy life expectancy prediction data. Data is generated, according to the medical fee bill data sorting steps 93 and the healthy life expectancy prediction data generating steps 94. Health screening report data and medical fee bill data necessary for carrying out the steps 93 and 94 are retrieved from the storage unit of health screening report data 171 and the storage unit of medical fee bill data 172, respectively. Healthy life expectancy prediction data thus generated is stored into the storage unit of healthy life expectancy prediction data 174.

Furthermore, the data integration step described in Embodiment 8 can also be carried out by the healthy life expectancy prediction data generating unit. Personal identification master data 131 necessary for carrying out this step is retrieved from the storage unit of personal identification master data 175.

Leaving off the explanation of the example of bringing the method for generating healthy life expectancy prediction data into effect by the system for generating healthy life expectancy prediction data, now, Embodiment 10 will be fully explained.

As described above, the present invention includes the healthy life expectancy prediction data generating unit that generates healthy life expectancy prediction data as the basic data for predicting healthy life expectancy from health screening report data, using the health screening report data stored in the storage unit of health screening report data and the medical fee bill data stored in the storage unit of medical fee bill data. A noticeable merit hereof is making it possible to generate healthy life expectancy prediction data differentiated by health screening report data, using only the information obtained when each person underwent health screening and when each person had medical services at any medical institution. Otherwise, such data generation would require a lot of labor and time.

While, in the above description of Embodiment 10, healthy life expectancy prediction data is generated, using the medical fee bill data stored in the storage unit of medical fee bill data, it is also possible to add a unit for generating other data. For example, a medical payment prediction knowledge data generating unit 176 for generating medical payment prediction knowledge data as the basic data for predicting medical payment from healthy life expectancy and a storage unit of medical payment prediction knowledge data 177 for storing generated medical payment prediction knowledge data are added. The unit 176 is specifically embodied in a general-purpose computer or the like. The storage unit 177 is specifically a database embodied in magnetic disks or other storage media, semiconductor memories, etc.

The medical payment prediction knowledge data is the basic data for predicting medical payment from healthy life expectancy; for example, data describing the transition of average medical payment a year for each person who underwent health screening, depending on age (graph 73) shown in FIG. 21. The medical payment prediction knowledge data generating unit generates medical payment prediction knowledge data, using the basic information (the person's date of birth) of medical fee bill data and charging information (charges). Generating this data is carried out, for example, in the following procedure.

First, the unit gets medical fee bill data from the storage unit of medical fee bill data; for age calculated from the basic information of the data (the person's date of birth), the unit obtains medical charges for one year for each person from the medical fee bill data records. Then, the unit sums up the medical charges from each bill data record per age. Finally, the unit divides the aggregate medical charges per age by the number of the persons to whom the bill data records belong. Thereby, average medical payment a year per person is obtained; that is, medical payment prediction knowledge data is obtained. The obtained medical payment prediction knowledge data is stored into the storage unit of medical payment prediction knowledge data.

As described above, the present invention includes the medical payment prediction knowledge data generating unit and the storage unit of medical payment prediction knowledge data. A noticeable merit hereof is making it possible to generate the basic data for predicting medical payment from healthy life expectancy as well as healthy life expectancy prediction data. Using this basic data for predicting medical payment in the medical payment prediction step and that step for recommended life-style improvement also befits each person who underwent health screening in making it possible to boot his or her will to prevent diseases and do self-healthcare.

Embodiment 11

Next, a preferred Embodiment 11 of the present invention will be described in detail, with reference to the appended drawings.

Figure 20:
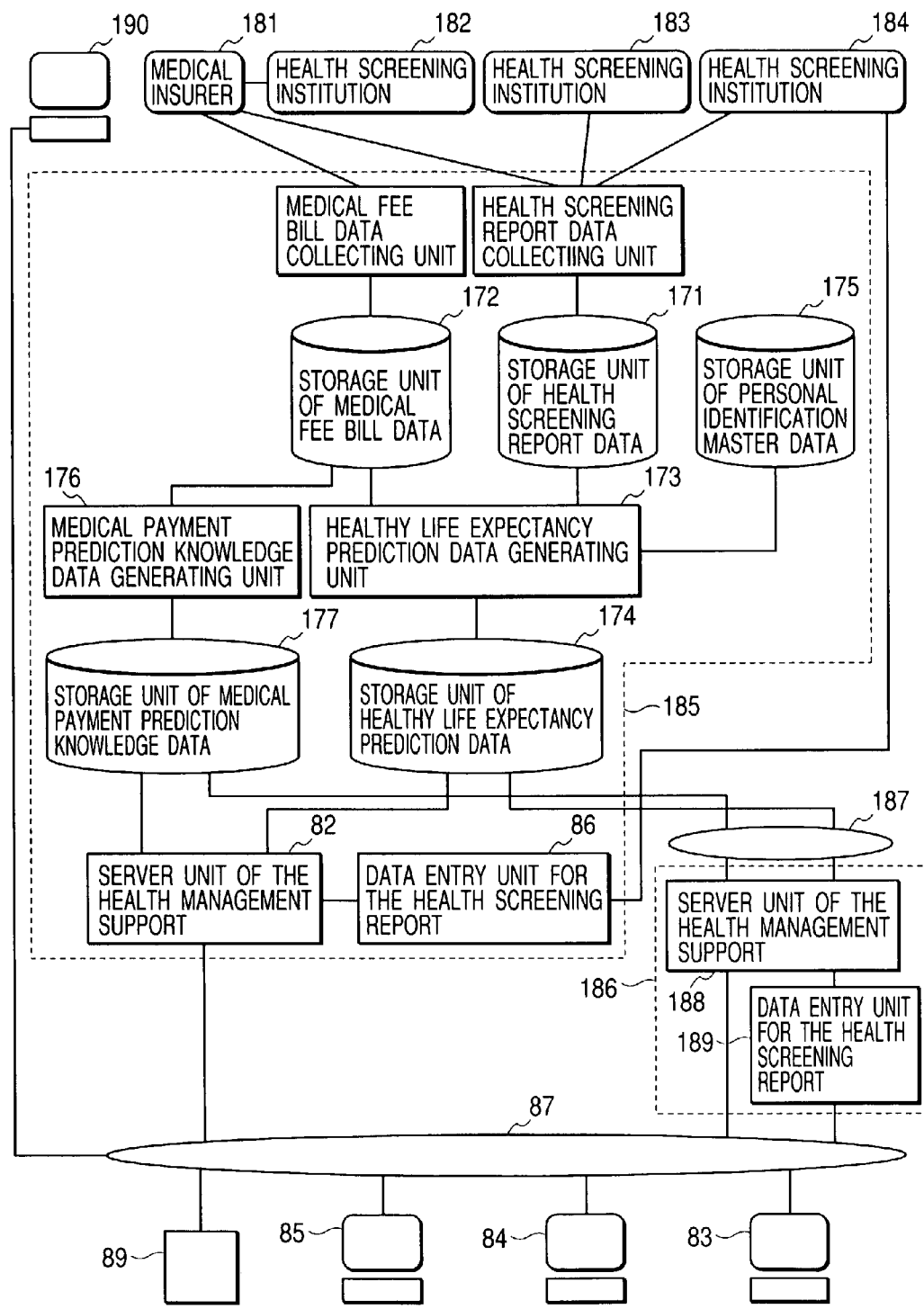
FIG. 20 is a diagram of an illustrative configuration of the health management support system of the present invention.

FIG. 20 is a diagram of an illustrative configuration of the health management support system of the present invention. Embodiment 11 is an illustrative health management system into which the health management support system (FIG. 12) described in Embodiment 9 and the system for generating healthy life expectancy prediction data (FIG. 19) described in Embodiment 10 are combined.

In FIG. 20, the components 82 to 87, 89, and 171 to 179 are the same as described in Embodiments 9 and 10. Reference numeral 181 denotes a medical insurer, 182 to 184 denotes medical screening institutions, 187 denotes a network, 188 denotes another server unit of health management support, 189 denotes a data entry unit for health screening reports, and 190 denotes a terminal for medical insurer. The storage unit of healthy life expectancy prediction data 174 and the storage unit of personal identification master data 177 correspond to the storage units 81 and 88 shown in FIG. 12. The healthy life expectancy prediction data and the medical payment prediction knowledge data generated in Embodiment 10 are stored into the two storage units (174 and 177) and retrieved to be used by the health management support system described in Embodiment 9.

Large area 185 defined with broken lines in FIG. 20 indicates the scope of the health management support system. In fact, a service operator such as a medical insurer, administrative organ, or a health management support service provider that is responsible for health management support possesses the system comprising the units within the above area and provides services such as providing information beneficial for health management support, such as health expectancy, and programs according to developed health management plans for assured persons, medical insurers, health screening institutions, etc.

Specifically, the system collects health screening report data and medical fee bill data from medical insurers and health screening institutions and generates healthy life expectancy prediction data. Using the health screening report data input through the data entry unit for health screening reports 86, the system estimates a predicted period of healthy life expectancy for each person who underwent health screening and displays the predicted period and related information on the terminal unit 83 (presents them to each person). Using the medical fee bill data, the system predicts change in medical payment by extended healthy life expectancy and displays this result on the terminal unit 190 (presents it to the medical insurer concerned). The data entry unit for health screening reports 86 receives health screening report data for each person who participates in the program of service provided by the service operator directly transmitted from the health screening institutions. For example, if the service operation makes a contract with a health screening institution 184 for such data supply, after a participant undergoes health screening at the health screening institution, his or her health screening report data is automatically transmitted to the above data entry unit and can be reflected in displaying healthy life expectancy information and other services.

Small area 186 defined with broken lines in FIG. 20 indicates the scope of another health management support system. This system uses the healthy life expectancy prediction data and the medial payment prediction knowledge data generated by the health management support system within the area 185 to provide information and services for health management support. Based on the above prediction and knowledge data, the service operator operating the health management support system within the area 186 can manipulate the data in their own method of prediction different from the service provider's one 185 and combine the data with other information. In view hereof, possible services include, for example, providing information that is more beneficial and developing health management plans suitable for a specific area, occupation, age range, etc. Arrangements can be made so that the service provider 185 can charge another service provider for the use of the prediction data that their system has generated.

The data entry unit for health screening reports 189 allows a person who underwent health screening to directly enter his or her health screening report data and transmit the data to the system over the network 187. For example, the person may enter such data with the keyboard or data may be input by reading from a medium (IC card, optical card, etc.) containing such data distributed from a health screening institution. It is advisable to apply a special information security function for transmitting data of high added value to the transmission over the network 187.

The features of the present invention are as follows:

A health management support system comprising: a storage unit of healthy life expectancy prediction data in which healthy life expectancy prediction data is stored as basic data for predicting healthy life expectancy; a server unit of health management support that estimates a predicted period of personal healthy life expectancy and generates information about health management, based on the predicted period estimated; and terminal units on which at least the predicted period of healthy life expectancy estimated by the server unit of health management support is displayed.

The health management support system wherein the server unit of health management support performs its function by carrying out the steps of the health management method as will be recited in the appended claims 1 to 8.

A method for predicting healthy life expectancy prediction data comprising: health screening report data collecting steps for collecting a diversity of health screening report data for a plurality of persons who underwent health screening; medical fee bill data collecting steps for collecting medical fee bill data, each of which comprises medical services details and charges for medical services rendered by a medical institution or the like to a person who underwent health screening; medical fee bill data sorting steps for sorting the collected medical fee bill data, according to the results specified in the health screening report data; and a healthy life expectancy prediction data generating step which comprises calculating the percent of the dead and the percent of people being sick or disabled for every age from the sorted medical fee bill data and generating healthy life expectancy prediction data as the basic data for predicting healthy life expectancy, based on the results of the calculation.

The method for predicting healthy life expectancy prediction data wherein the medical fee bill data sorting steps comprise setting sorting conditions beforehand, based on the results specified in the health screening report data, and automatically sorting the medical fee bill data collected in the medical fee bill data collecting steps by the set sorting conditions.

The method for predicting healthy life expectancy prediction data wherein the healthy life expectancy prediction data generating step further comprises setting conditions beforehand by which to determine that a person is so sick or disabled as to be difficult to live without help from medical services details included in medical fee bill data records and automatically counting patients out of the medical fee bill data by the set conditions.

The method for predicting healthy life expectancy prediction data further comprising a data integration step which comprises interlinking health screening report data and medical fee bill data for each person who underwent health screening, using person-identifiable specifications included in each record of health screening report data collected in the health screening report data collecting steps and person-identifiable specifications included in each record of medical fee bill data collected in the medical fee bill data collecting steps.

A system for generating healthy life expectancy prediction data comprising: a storage unit of health screening report data in which a diversity of health screening report data for a plurality of persons who underwent health screening is stored; a storage unit of medical fee bill data in which medical fee bill data comprising a diversity of medical services details and charges to a plurality of customers of medical institutions is stored; a healthy life expectancy prediction data generating unit that generates healthy life expectancy prediction data as basic data for predicting healthy life expectancy, using the health screening report data stored in the storage unit of health screening report data and the medical fee bill data stored in the storage unit of medical fee bill data; a storage unit of healthy life expectancy prediction data in which generated healthy life expectancy prediction data is stored.

The system for generating healthy life expectancy prediction data wherein the healthy life expectancy prediction data generating unit performs its function by carrying out the above-recited steps of the method for generating healthy life expectancy prediction data.

The foregoing health management support system wherein the system employs the storage unit of healthy life expectancy prediction data included in the system for generating healthy life expectancy prediction data.

A health management support method as will be recited in the appended claims 1 to 8 wherein healthy life expectancy prediction data for use in the personal healthy life expectancy prediction data generating step is generated by carrying out the healthy life expectancy prediction data generating step of the foregoing method for generating healthy life expectancy prediction data.

As described above, the health management support system of the present invention estimates predicted healthy life expectancy periods from health screening report data for each person who underwent heath screening and medical fee bill data and displays the above periods and related information, wherein the health screening report data is collected from health screening institutions or input by each person and the medical fee bill data is collected from medical insurers. A noticeable point of the benefit hereof is enabling each person who underwent health screening to grasp his or her health condition quantitatively, based on the index of healthy life expectancy, and making it possible to develop health management plans based on healthy life expectancy and predict health management effects, which could boost the person's will to prevent diseases and do self-healthcare.

As described above, the health management support method and system of the present invention are intended to estimate predicted healthy life expectancy periods for each person who underwent health screening, based on health screening report data for each person, and use the above periods and related information for health management support. The method and system for generating healthy life expectancy prediction data included in the present invention are intended to generate healthy life expectancy prediction data differentiated by health screening report data from a diversity of health screening report data and medical fee bill data. The above methods, systems, and components thereof may be changed or modified in different forms without departing from the essential characteristics thereof.

As described above, the primary merit of the present invention is estimating predicted healthy life expectancy periods from health screening report data for each person who underwent heath screening and medical fee bill data and displaying the above periods and related information, wherein the health screening report data is collected from health screening institutions or input by each person and the medical fee bill data is collected from medical insurers. A noticeable point of the usefulness of the invention is enabling each person who underwent health screening to grasp his or her health condition quantitatively, based on the index of healthy life expectancy, and making it possible to develop health management plans based on healthy life expectancy and predict health management effects, which could boost the person's will to prevent diseases and do self-healthcare.

The present invention may be embodied in other specific forms without departing from the spirit or essential characteristics thereof. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within the scope of the claims.

What is claimed is:

1. A health management support method implemented in a computer-based data processing system for generating life expectancy data to be used in a health management system, comprising:
    providing a database for storing healthy life expectancy prediction data that represents transition of a percentage of normal people in each result of health screening;
    generating health screening report data for each person who undergoes health screening by data entry means;
    generating personal healthy life expectancy prediction data by selecting at least one of said healthy life expectancy prediction data from said database in combination of at least one of daily living habits and at least one of decision results in said inputted health screening report data for each said person;
    estimating a predicted period of healthy life expectancy of each said person by selecting one of said healthy life expectancy data from said database in accordance with said at least one of daily living habits and said at least one of decision results in said health screening data of said person who undergoes health screening and calculating based on said selected personal healthy life expectancy prediction data;
    outputting said estimated predicted period of healthy life expectancy of each said person,
    preparing medical payment prediction knowledge data as basic data for predicting medical payment from a diversity of healthy life expectancy; and
    calculating a predicting amount of future medical payment of the each person who undergoes health screening based on the predicted period of healthy life expectancy of the each person and the medical payment prediction knowledge data;

wherein a predicting amount of future medical payment is calculated by the summation of the average medical expenses a year per age multiplied by correction coefficients for the predicted duration of disease and/or disability that is difference between an averane life expectancy and the predicted period of healthy life expectancy, the correction coefficients being set so as to decrease the average medical expenses a year per age as the recuperation period is prolonged.

2. A health management support method as recited in claim 1, further comprising:
a health management plan generation step which comprises generating health management plans for each said person who underwent health screening, based on the predicted value of healthy life expectancy of each said person.

3. A health management support method as recited in claim 2, wherein the health management plan generation step comprises generating health screening recommendation plans.

4. A health management support method as recited in claim 2, wherein the health management plan generation step further comprises generating healthy lifestyle practice recommendation plans for guiding each person in improving his or her living habits such as meals, exercise, and smoking.

5. A health management support method as recited in claim 4, further comprising:
a health management effect prediction step which comprises estimating change to the predicted period of healthy life expectancy of a person,
wherein the expected change is based on the person practicing life-style improvement advised in a health management plan generated in the health management plan generation step.

6. A health management support method as recited in claim 5, further comprising:
a medical payment prediction step which comprises preparing medical payment prediction knowledge data beforehand as basic data for predicting medical payment from a diversity of healthy life expectancy and calculating change to medical payment predicted for a person who underwent health screening, based on the change to the predicted period of healthy life expectancy of the person estimated in the health management effect prediction step and through the use of the medical payment prediction knowledge data.

7. A health management support method as recited in claim 1, further comprising:
a medical insurer management support step which comprises predicting aggregate medical payment of a medical insurer as a whole, based on the predicted period of healthy life expectancy of each assured person who is a policyholder insured by the medical insurer.

8. The health management support method according to claim 1, wherein said calculation is performed by applying an equation $$\sum_{x=1}^{\infty} Lx/Li$$

to select said healthy life expectancy prediction data when age of said person is i, wherein Lx and Li are percents of normal people at age x and age i, respectively.

9. The health management support method according to claim 1, wherein said healthy life expectancy prediction data is generated by collecting health screening report data of a plurality of person, collecting medical data comprised of medical services details, generating a healthy life expectancy prediction data by calculating the percentage of the dead and the percentage of people being sick or disabled for every age from said medical data, and generating healthy life expectancy prediction data.

10. The health management support method according to claim 9, wherein medical data has medical fee bill data.

11. A health management support program implemented in software embodied on a computer-readable medium for generating life expectancy data to be used in a health management system, said program comprising the steps of:
providing a database for storing healthy life expectancy prediction data that represents transition of a percentage of normal people in each result of health screening;
generating health screening report data for each person who undergoes health screening by data entry means;
generating personal healthy life expectancy prediction data by selecting at least one of said healthy life expectancy prediction data from said database in combination of at least one of daily living habits and at least one of decision results in said inputted health screening report data for each said person;
estimating a predicted period of healthy life expectancy of each said person by selecting one of said healthy life expectancy data from said database in accordance with said at least one of daily living habits and said at least one of decision results in said health screening data of said person who undergoes health screening and calculating based on said selected personal healthy life expectancy prediction data; and
outputting said estimated predicted period of healthy life expectancy of each said person,
preparing medical payment prediction knowledge data as basic data for predicting medical payment from a diversity of healthy life expectancy; and
calculating a predicting amount of future medical payment of the each person who undergoes health screening based on the predicted period of healthy life expectancy of the each person and the medical payment prediction knowledge data,
wherein a predicting amount of future medical payment is calculated by the summation of the average medical expenses a year per age multiplied by correction coefficients for the predicted duration of disease and/or disability that is difference between an average life expectancy and the predicted period of healthy life expectancy, the correction coefficients being set so as to decrease the average medical expenses a year per age as the recuperation period is prolonged.

12. A health management support program as recited in claim 11, further comprising:
a health management plan generation step which comprises generating health management pians for each said person who underwent health screening, based on the predicted value of healthy life expectancy of each said person.

13. A health management support program as recited in claim 12, wherein the health management plan generation step comprises generating health screening recommendation plans.

14. A health management support program as recited in claim 12, wherein the health management plan generation step further comprises generating healthy lifestyle practice recommendation plans for guiding each person in improving his or her living habits such as meals, exercise, and smoking.

15. A health management support program as recited in claim 14, further comprising:

a health management effect prediction step which comprises estimating change to the predicted period of healthy life expectancy of a person, wherein the expected change is based on the person practicing life-style improvement advised in a health management plan generated in the health management plan generation step.

16. A health management support program as recited in claim 15, further comprising:

a medical payment prediction step which comprises preparing medical payment prediction knowledge data beforehand as basic data for predicting medical payment from a diversity of healthy life expectancy and calculating change to medical payment predicted for a person who underwent health screening, based on the change to the predicted period of healthy life expectancy of the person estimated in the health management effect prediction step and through the use of the medical payment prediction knowledge data.

17. A health management support program as recited in claim 11, further comprising:

a medical insurer management support step which comprises predicting aggregate medical payment of a medical insurer as a whole, based on the predicted period of healthy life expectancy of each assured person who is a policyholder insured by the medical insurer.

18. The health management support method as recited in claim 1, comprising: calculating predicted duration of at least one of diseases and disability based on said predicted period of said healthy life expectancy, and calculating an aggregate of medical payments predicted for the at least one of diseases and disability.

19. The health management support method as recited in claim 1, further comprising: collecting medical fee bill data;

sorting said medical fee bill data according to the results specified in the health screening report data;

calculating the percentage of the dead and the percentage of people being sick or disabled for each age from said stored medical fee bill data; and generating said healthy life expectancy prediction data corresponding to the sorted results based on said calculation.

20. The health management support method as recited in claim 1, wherein said daily living habit is at least one of smoke, drink, and exercise, and said decision result is at least one of hyper-tension, hyper-lipemia, and hyper-glycemia.

* * * * *